United States Patent [19]

Bianco et al.

[11] Patent Number: 5,856,115
[45] Date of Patent: Jan. 5, 1999

[54] ASSAY FOR IDENTIFICATION THERAPEUTIC AGENTS

[75] Inventors: James A. Bianco, Seattle; Stuart L. Bursten, Snoqualmie; Jack W. Singer, Seattle, all of Wash.

[73] Assignee: Fred Hutchinson Cancer Research Center, Seattle, Wash.

[21] Appl. No.: 196,878

[22] Filed: Feb. 14, 1994

Related U.S. Application Data

[63] Continuation of Ser. No. 888,722, May 26, 1992, abandoned, which is a continuation-in-part of Ser. No. 732,227, Jul. 16, 1991, abandoned, which is a continuation-in-part of Ser. No. 704,992, May 24, 1991, abandoned.

[51] Int. Cl.$^6$ ..................................................... C12Q 1/48
[52] U.S. Cl. .............................................. 435/15; 514/263
[58] Field of Search ....................... 435/15, 18; 514/263, 514/929; 544/267, 271

[56] References Cited

U.S. PATENT DOCUMENTS

| | | | |
|---|---|---|---|
| 3,422,107 | 1/1969 | Mohler et al. ........................... | 260/256 |
| 4,515,795 | 5/1985 | Hinze et al. ............................. | 514/263 |
| 4,576,947 | 3/1986 | Hinze et al. ............................. | 514/263 |
| 4,636,507 | 1/1987 | Kreutzer et al. ........................ | 514/263 |
| 4,965,271 | 10/1990 | Mandell et al. ........................ | 514/263 |
| 5,096,906 | 3/1992 | Mandell et al. ........................ | 514/263 |
| 5,112,827 | 5/1992 | Saunders et al. ....................... | 514/263 |
| 5,118,500 | 6/1992 | Hänel et al. ............................ | 414/85.1 |
| B1 3,373,433 | 6/1973 | Mohler et al. .......................... | 544/271 |

OTHER PUBLICATIONS

Davis et al., *Applied Environment. Microbiol.* 48:327, 1984.
Bianco et al., *Blood* 78:1205, 1991.
DosReis et al., *Cellular Immunology,* vol. 101, No. 1, "Purinergic Modulation of T–Lymphocyte Activation: Differential Susceptibility of Distinct Activation Steps and Correlation with Intracellular 3', 5'–Cyclic Adenosine Monophosphate Accumulation", pp. 213–231, 1986.
Davis, P.J., Microbial Models of Mammalian Metabolism . . . APP and Environ Micro, vol. 48 No. 2 1984, pp. 327–331.

*Primary Examiner*—Ralph Gitomer

[57] ABSTRACT

There is disclosed a method for screening for inhibitors of cellular second messenger signaling regulated by lysophosphatidic acid acyl transferase (LPAAT) and phosphatidic acid phosphohydrolase (PAPH), which method comprises contacting target cells or appropriate subcullular elements under appropriate conditions of stimulation with a candidate drug and assessing the levels of the relevant subsets of phosphatidic acid (PA) and diacylglycerol (DAG) in the presence and absence of the candidate drug.

4 Claims, 22 Drawing Sheets

ASSAY FOR IDENTIFICATION THERAPEUTIC AGENTS

This is a Continuation of application No. Ser. 07/888,722, filed May 26, 1992, now abandoned which in turn is a continuation-in-part of application No. Ser. 07/732,227, filed Jul. 16, 1991, now abandoned which is a continuation-in-part of application No. Ser. 07/704,992, filed on May 24, 1991 now abandoned.

This invention was made in part with government support under National Institutes of Health Grant HL31782. The government has certain rights in this invention.

TECHNICAL FIELD

The invention relates to modulation of cellular responses to external stimuli by control of the short-term secondary responses to primary cell-affecting agents. More specifically, the invention concerns the use of xanthine derivatives to control elevations in the level of specific sn-2 unsaturated phosphatidic acid and the corresponding phosphatidic acid-derived diacylglycerol which occur in response to these stimuli.

BACKGROUND ART

The general outlines of the mechanisms by which external stimuli effect the behavior of target cells have been described in general Molecular Biology textbooks over the last 10–20 years. For at least some of these stimuli, a primary interaction of the stimulating agent at a cell surface receptor is translated into an effect on various secondary signaling pathways internal to the cell, which secondary signaling pathways in turn produce the observed effect on cellular behavior. Most of these secondary pathways involve the synthesis and hydrolysis of phosphorylated acyl glycerol derivatives such as phosphatidic acid, phosphatidyl inositol, phosphatidyl ethanolamine, lysophosphatidic acid, and so forth. The synthesis and release of the components of these compounds can result in cellular proliferation, suppression of proliferation, differentiation, activation, and so forth, depending upon the nature of the target cell and the stimulus applied.

The pathways regulating the synthesis and degradation of phosphorylated derivatives of acyl glycerols are complex and interlocking. Certain effects of external stimuli are seen immediately—i.e., within a few seconds or a minute; others are seen 30–60 minutes after the external stimulus has bound to the surface receptor of the cell. It is believed that the short-term effects on these second messengers are associated with the stimulus itself and are not appreciably interconnected with those aspects of the phosphorylated acyl glycerol (PAG) pathways that regulate normal cellular processes.

As demonstrated hereinbelow, a short-term effect of a primary stimulus on a target cell is to elevate the levels of specific unsaturated subspecies of phosphatidic acid (PA) and the corresponding diacylglycerol (DAG) formed by the hydrolysis of this PA. It is known that DAG may be generated by other secondary mechanisms such as the hydrolysis of phosphatidyl inositol (PI) or phosphatidyl ethanolamine (PE). However, the nature of the acyl groups of the DAG derived from these various sources is not identical. In particular, DAG derived from PA hydrolysis has a high level of sn-2 unsaturation not containing arachidonate (C20:4).* Typical fatty acid residues found in these

*This notation refers to the number of C in the acyl residue (20) and the number of π bonds (4). PA/DAG subsets include those of oleic (C18:1), linoleic (C18:2) and docosahexanenoyl (C22:6).

Further explanation of the model of cell activation and its relation to the compounds of the invention as found by applicants is set forth hereinbelow.

There are a large number of contexts in which it is desirable to protect target cells from primary stimuli which are the result of, for example, disease states (such as malignancy, autoimmune diseases, or infection) or of medical intervention (such as bone marrow transplantation or chemotherapy) which have negative sequelae in the target cell. This protection can be achieved by the method of the invention.

Some of the compounds useful in the method of the invention have been suggested for medical use in other contexts. Pentoxifylline (1-(5-oxohexyl-3,7-dimethylxanthine) is one member of this class of xanthine derivatives which has seen widespread medical use for the increase of blood flow. Pentoxifylline and its use as a vasodilator are disclosed in U.S. Pat. Nos. 3,422,307 and 3,737,433. The nature of the metabolism of pentoxifylline was summarized by Davis, P. J. et al., *Applied Environment Microbiol* (1984) 48:327–331. Some of the metabolites are also among the compounds of the invention. The immediate reduction product which is the primary metabolite of pentoxifylline—1-(5-hydroxyhexyl)-3, 7-dimethyxanthine—was disclosed to increase cerebral blood flow in U.S. Pat. Nos. 4,515,795 and 4,576,947.

In addition, a number of patents have issued on the use of tertiary alcohol analogs to compounds of this class in enhancing cerebral blood flow. These include U.S. Pat. Nos. 4,833,146 and 5,039,666.

Furthermore, U.S. Pat. No. 4,636,507 describes the ability of pentoxifylline and its primary metabolite to stimulate chemotaxis in polymorphonuclear leukocytes in response to a known stimulator of chemotaxis. The ability of pentoxifylline and related tertiary alcohol substituted xanthines to inhibit the activity of certain cytokines on chemotaxis is disclosed in U.S. Pat. No. 4,965,271 and U.S. Pat. No. 5,096,906. Administration of pentoxifylline and GM-CSF decrease tumor necrosis factor levels in patients undergoing allogeneic bone marrow transplant (Bianco, J. A. et al., *Blood* (1990) 76:Supplement 1 (522A). The reduction in assayable levels of TNF was accompanied by a significant reduction in transplant-related complications. However, in normal volunteers, TNF levels are higher among PTX recipients. It does not, therefore, appear that elevated levels of TNF are the primary cause of such complications.

It has now been found that the compounds described hereinbelow can be used systematically to maintain the homeostasis of a large number of target cells in response to a variety of stimuli. In addition, routes to administer such compounds which permit effective dosages to be provided are disclosed.

DISCLOSURE OF THE INVENTION

The invention is directed to the use of substituted xanthines in modulating cellular response to external or in situ primary stimuli, as well as to specific modes of administration of such compounds in effective amounts.

Thus, in one aspect, the invention is directed to a method to modulate the response of a target cell to a stimulus, which method comprises contacting said cell with an amount of a compound of the formula

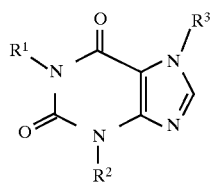

$$\text{(I)}$$

wherein one and only one of $R^1$ and $R^3$ is a straight-chain or branched-chain ω- or (ω-1)-hydroxyalkyl(5–8C), or is an (ω-1)-oxoalkyl(5–8C) or is an (ω,ω-1) or (ω-1,ω-2)-dihydroxyalkyl(5–8C), or is an alkenyl substituent (5–8C), and the other is alkyl (1–12C) optionally containing one or two non-adjacent oxygen atoms in place of C, and wherein $R^2$ is alkyl (1–12C) optionally containing one or two non-adjacent oxygen atoms in place of C.

When a cell is stimulated, elevated levels of a subset of phosphatidic acid (PA) containing sn-2 non-arachidonate unsaturation and diacylglycerol (DAG) derived from this PA are caused to form in the short term by the stimulating agent. Compounds of formula I effect a diminution in these elevated levels, and the diminution is equal to or greater than the diminution effected by treating the cells with pentoxifylline (PTX) at a concentration of 0.5 mM. The result is to modulate the response of the target cell to the stimulus. As further explained hereinbelow, this effect, analogous to that of pentoxifylline, results from blockage of a specific activation pathway that does not involve phosphatidyl inositol (PI) but rather derives from phosphatidic acid that is largely composed of 1,2-diunsaturated and 1-alkyl, 2-unsaturated species. These compounds, like pentoxifylline, are shown to inhibit the enzymes involved in this pathway.

In other particular aspects, the invention is directed to methods to decrease proliferation of tumor cells in response to an activated oncogene; to stimulate hematopoiesis in the presence of agents which inhibit hematopoiesis, such as chemotherapeutic agents; to methods to suppress the activation of T-cells in the presence of antigen and the secretion of antibodies by B-cells in the presence of antigen; to suppress the activation of macrophage by endotoxins or GM-CSF; to enhance the resistance of mesenchymal cells to tumor necrosis factor; to inhibit the proliferation of smooth muscle cells in response to growth factors; to inhibit the activation of T-cells and viral replication in response to human immunodeficiency virus; to inhibit the proliferation of kidney mesangial cells in response to IL-1; and to enhance the proliferation of bone marrow stromal cells in response to tumor necrosis factor.

The cells to be affected may either be contacted with the compound of Formula I in vitro culture, in an extracorporeal treatment, or by administering the compound of Formula I or mixtures thereof to a subject whose cells are to be affected.

In still another aspect, the invention is directed to a method to administer the compounds of the invention to a mammalian subject comprising coadministering an effective amount of an agent which reduces the activity of the enzyme P450. In particular, coadministration of the compounds of the invention along with a quinolone enhances their effect.

In still another aspect, the invention is directed to a method to assess the effects of candidate drugs on the secondary signaling pathway regulated by lysophosphatidic acid acyl transferase (LPAAT) and phosphatidic acid phosphohydrolase (PAPH) by contacting target cells or appropriate subcellular elements under appropriate conditions of stimulation with the candidate drug and assessing the levels of the relevant subsets of PA and DAG in the presence and absence of the drug.

BRIEF DESCRIPTION OF THE DRAWINGS

FIG. 1 shows the HPLC trace of cells in resting condition.

FIG. 2 shows the HPLC from cells stimulated with IL-1 after 5 seconds.

FIG. 3 shows the HPLC trace derived from cells stimulated with IL-1 for 15 seconds.

FIG. 4 shows the HPLC trace derived from cells stimulated with IL-1 for 60 seconds.

FIG. 5 shows the HPLC trace derived from cells after stimulation for 15 seconds with IL-1 in the presence of 100 μM pentoxifylline.

FIG. 6 shows the HPLC trace derived from cells after stimulation for 60 seconds with IL-1 in the presence of 100 μM pentoxifylline.

FIG. 7 shows the HPLC trace derived from cells after stimulation for 15 seconds with IL-1 in the presence of 500 μM pentoxifylline.

FIG. 8 shows the HPLC trace derived from cells after stimulation for 15 seconds with IL-1 in the presence of 1 mM pentoxifylline.

FIG. 9 shows the HPLC trace derived from cells after stimulation for 30 seconds with IL-1 in the presence of 1 mM pentoxifylline.

FIG. 10 shows the HPLC trace derived from cells after stimulation for 45 seconds with IL-1 in the presence of 1 mM pentoxifylline.

FIG. 11 shows the HPLC trace derived from cells after stimulation for 60 seconds with IL-1 in the presence of 1 mM pentoxifylline.

MODES OF CARRYING OUT THE INVENTION

Figure 1:
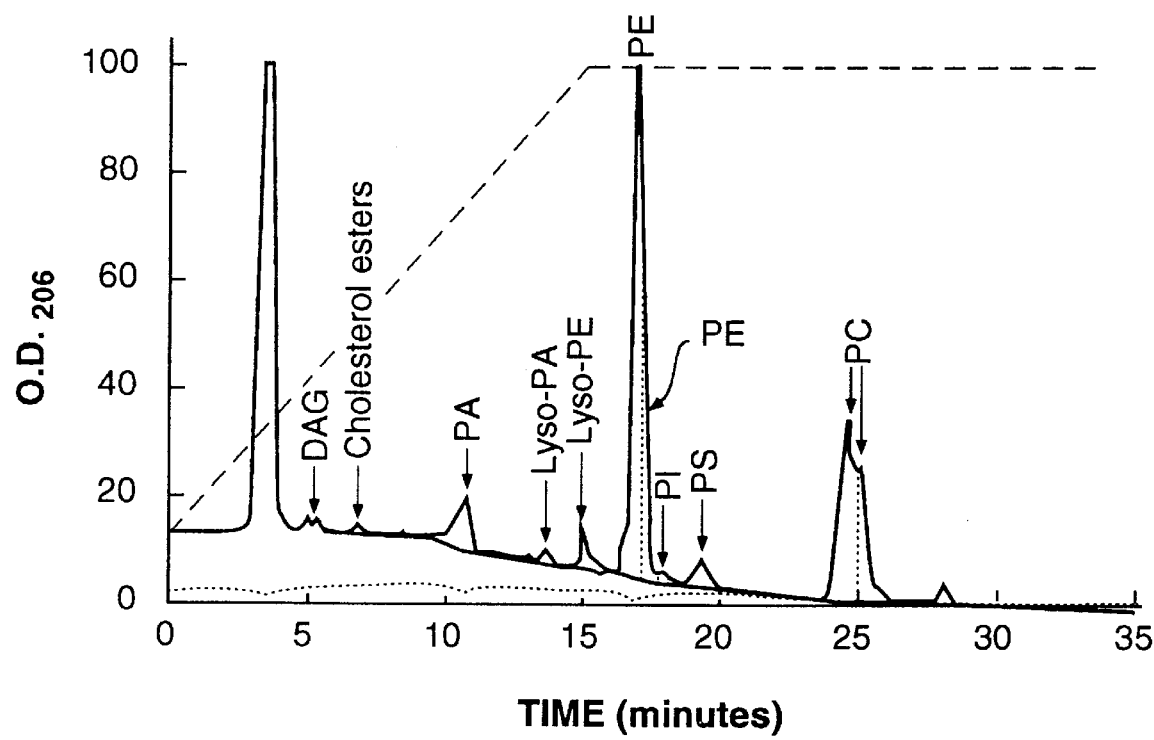
FIGS. 1–11 show elution patterns obtained from high pressure liquid phase chromatography (HPLC) of lipids extracted from human glomerular mesangial cells under various conditions of stimulation with IL-1 and treatment with pentoxifylline.
Figure 2:
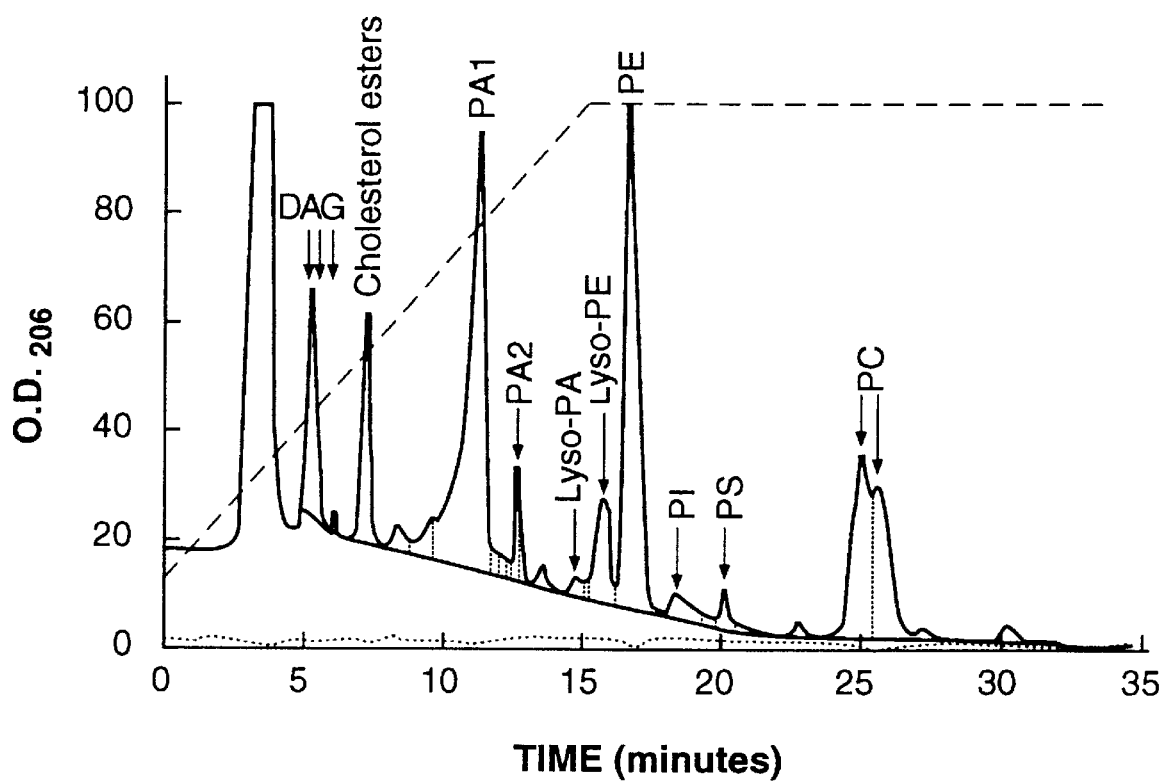

The invention is directed to methods of controlling cellular behavior which take advantage of the effect of certain xanthine derivatives on a particular phase of the secondary messenger pathway system. In particular, this aspect of the pathway is summarized in the following diagram, which uses the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=Phosphatidyl choline
"remodeled" PA, cyclic pathway=PAA, LPA, PA and DAG intermediates substituted with L-saturated, 2-linoleoyl- or 1,2-dileolyl/1,2-sn-dilinoleoyl at the indicated sni and sn2 positions.
"Classical PI Pathway"=PI, DAG, PA intermediates substituted with 1-stearoyl, 2-arachidonbyl fatty acyl side chains.
"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

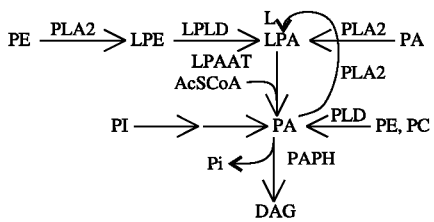

As shown in the above diagram, lysophosphatidase acyl transferase catalyzes the synthesis of phosphatidic acid from lysophosphatidic acid by incorporation of an acyl group from acyl CoA. Hydrolysis of the phosphate moiety by PA phosphohydrolase results in the formation of DAG. These aspects of the pathway appear to be activated immediately (within a minute) upon stimulation by a primary stimulus acting at the receptor on the cellular surface. The immediate detectable effect, as shown hereinbelow, is an elevation of levels of PA and DAG. Administration of the compounds of the invention reverse this elevation.

The inventors herein have shown that each membrane phospholipid subclass such as PA, PI, PE, phosphatidyl choline (PC) and phosphatidyl serine (PS) reaches a stable content of characteristic fatty acyl side chains due to cyclic remodeling of the plasma membrane as well as turnover for each subclass. PA is quite stable and present in small quantities. PA in resting cells is largely saturated, containing a significant amount of myristate, stearate and palmitate. In representative resting cells, PC consists mostly of acyl palmitate in the sn-1 position and oleate in the sn-2 position. PE and PI are predominantly composed of sn-1 stearate and sn-2 arachidonate. Due to this characteristic content of acyl groups in the sn-1 and sn-2 positions, the origin of any PA species may be deduced from the nature of the acyl groups—e.g., if PA is derived from PC through the action of PLD, it will contain the characteristic acyl side chains of PC substrate processed through this pathway. Further, due to this characteristic sn-1 and sn-2 acyl content, the origin of any 1,2,sn-substrate species may be differentiated as to its origin. This is qualified by the necessity of knowing whether or not the phospholipid species passes through a PA form previous to hydrolysis to DAG. As shown above, the lyso-PA which that is converted to phosphatidic acid and thence to DAG may be shown. The complexities of these pathways can be sorted by suitable analysis of the fatty acyl side chain types of intermediate in cells at various times after stimulation.

It has been demonstrated by the inventors herein that in certain mesenchymal cells, such as neutrophils and rat/human mesangial cells several secondary signaling pathways may be activated in tandem, simultaneously or both. For example, in neutrophils, F-Met-Leu-Phe stimulates formation of PA through the action of PLD, followed in time by formation of DAG through the action of PAPH; then several minutes later, DAG is generated from PI through the classical phosphoinositide pathway. In many of the cells examined, DAG is derived from both PA that is being remodeled through a cycle whereby PAA is sn-2 hydrolyzed by PLA-2, followed by sn-2 transacylation by LPAAT, and a PLD-pathway from PA that is generated from either PE or PC substrates by PLD.

As the methods developed by the inventors herein have permitted the differentiation of the various subspecies of, for example, PA and DAG, it has been found that several subspecies are sometimes formed simultaneously. For example, in rat glomerular epithelial cells after stimulation with IL-1, three different DAG species are formed, one derived from PA remodeled by the remodeling mechanism described above involving LPAAT, one derived from PA derived from PLD, and one derived from PI. The "remodeled" PA is characterized as 1-saturated, 2-linoleoyl PA, and 1,2-dioleolyl/1,2-sn-dilinoleoyl PA. The DAG derived from these PAs has the latter fatty acyl sidechain composition as confirmed by mass spectrometry. The DAG derived from PI is largely 1-stearoyl, 2-arachidonoyl and separates from the PA-derived DAG.

The compounds of the invention, including inhibitors of subspecies of LPAAT in PAPH enzymes with substrate specificity for intermediates with 1,2-diunsaturated and 1-alkyl,2-unsaturated subspecies. One representative example of such an inhibitor is pentoxifylline, as shown herein, that blocks PAPH in a specific activation pathway that does not involve PI but rather derives from phosphatidic acid that is largely composed of 1,2-diunsaturated and 1-alkyl,2-unsaturated subspecies. This is shown, for example, by the demonstration that human mesangial cells stimulated with TNF produce DAG from PI and regenerate PI in the absence and the presence of pentoxifylline. In the latter system there is no evidence to suggest that PA or DAG are derived from sources other than PI. The HPLC tracing and mass spectrometry techniques of the present invention permit subtle, complex evaluation of the formation of PI and DAG subspecies which are uniform and relatively monotonous, i.e., one type of signaling molecule not several, consonant with a consistent, non-radiating type of signal.

It is thus shown that different concentrations of pentoxifylline specifically blocks formation of remodeled PA through the PA/DAG pathway; namely, 1) at high PTX concentrations by blocking formation of PA subspecies at LPAAT; 2) at low PTX concentrations by blocking the formation of PA-derived DAG at PAPH. In the presence of pentoxifylline PA continues to form through the action of phospholipase D, and DAG is also formed through the action of phospholipase C on PC and PI. The latter pathways are not inhibited by the compounds of the invention or pentoxifylline. In pentoxifylline-treated cells, DAG derived from remodeled and PLD-generated PA is diminished, for example, 1,2-sn-dioleoyl DAG, 1-alkyl, 2-linoleoyl DAG and 1-alkyl,2-docosahexaneoyl DAG.

In general, the specific relevant PA and corresponding DAG measured by the invention assay and affected by the compounds of Formula I are referred to generally as having fatty acyl sidechain in the sn-1 and sn-2 positions that are unsaturated and non-arachidonate.

The ability of the assay system of the invention to detect these specific intermediates of PA and DAG permits discrimination of the relevant substrates and enzymes that constitute the novel pathway for alternative phospholipid metabolism that is a subject of the invention.

Assays for developing new therapeutic agents, based upon the present disclosure, are set forth in detail below. Briefly, since the metabolic enzymes involved in the subject alternative phospholipid metabolic pathway exhibit exquisite stereospecificity for different acyl sidechains and isomeric forms of substrates, drugs with improved therapeutic efficacy and potency can be provided by using drug preparations enriched in particular enantiomeric forms of PTX and its metabolites.

It is contemplated that the different enantiomeric variants (e.g., stereoisomers and chiral forms) of the xanthines will have different drug activities, based upon their differential ability to inhibit phosphatidate phosphohydrolase. The chain length of the alkyl group $R^1R^5$, and/or the structure of the $R^4R^5$ (e.g., 2-hydroxypropyl) ternary hydroxylalkylxanthines of Formula II can have asymmetric carbon atoms and this can thus present different stereoisomers. Thus, the invention contemplates that in one preferred embodiment selected chiral forms of the M1, metabolic variant of xanthine have improved drug activity. For example, Singer et al., *Bone Marrow Transplantation* (in press) discloses: (a) data relating to metabolites M1, M3, M4, and M5 and two analogs HWA448 and HWA138—how the metabolites might exhibit greater activity than PTX; (b) M1 and HWA448 are active; M3, M4 and M5 and HWA138 produced minimal or no suppression of T cell proliferation; (c) length of the N1 sidechain in PTX and the size of the N7 substitutions were important for this activity; (d) adding PTX after triggering lymphocytes in a mixed lymphocyte culture was still effective in blocking a proliferative response; (e) PTX suppressed proliferation of lymphocytes induced by anti-CD3 and inhibition was mediated through a mechanism other than TNFA or IL-1 because addition of exogenous recombinant TNF or IL-1 did not reverse the inhibition; (f) PTX had a greater effect on secretion of TNFα than it did on down regulation of TNF transcription; and (g) PTX decreased expression of cell surface antigens on lymphocytes including HLA-DR, the transferrin receptor (CD71), the IL-2 receptor (CD25), and CD69 in MLR-stimulated lymphocytes.

The effect of the xanthine-derived compounds of the invention can be demonstrated in vitro and in vivo. As shown hereinbelow, a simple assay involving incubation of target cells with primary stimulus in the presence or absence of the xanthine derivative followed by extraction and analysis of lipid content is diagnostic of the levels of various members of the foregoing pathway as characterized by their fatty acyl content. This assay indirectly measures the effect of the xanthine derivative on the relevant enzymes lysophosphatidic acid acyltransferase (LPAAT) and phosphatidic acid phosphoryl hydrolase (PAPH). In general, inhibition of these enzymes is effected by the xanthine derivative, thus resulting in lowering of the levels of the relevant species of the particular acylated subspecies of PA and DAG intermediates.

It is shown in the examples hereinbelow that coadministration in vivo of pentoxifylline along with an inhibitor of P450 results in an enhanced effect of the pentoxifylline. It is believed that this effect in vivo is due to the inhibition of the metabolic pathway for the xanthine derivatives. While the basis for this effect may not be, and probably is not, the same in vitro, nevertheless, the foregoing assay is useful in assessing candidate drugs for coadministration with the xanthine-derived compounds useful in the invention. This is the case since it is also demonstrable in vitro that a compound capable of inhibiting P450, such as a quinolone, enhances the effect of the xanthine derivative, thus lowering the dosage levels required. An additional in vitro assay is described in Example 2 hereinbelow wherein a transformed cell line containing an activated oncogene is shown to be phenotypically modified by pentoxifylline wherein coadministration of pentoxifylline and ciprofloxacin has a dramatically better effect than either pentoxifylline or ciprofloxacin alone. Using such an assay, additional xanthine derivatives and P450 inhibitors may be tested for effectiveness of their combination in modulating cellular behavior.

The xanthine derivatives, alone or in combination with a P450 inhibitor, are effective in vivo to modulate cellular behavior. The desirability of coadministration of the xanthine derivative with the P450 inhibitor varies with the choice of xanthine derivative. For example, if pentoxifylline is used as a xanthine derivative, coadministration is highly desirable. If, on the other hand, the primary metabolite of pentoxifylline, 1-(5-hydroxyhexyl)-3,7-dimethylxanthine (designated M1 herein) is used, coadministration of the P450 inhibitor is not required.

Demonstrated hereinbelow is the effect of administering pentoxifylline in combination with a quinolone in reversing the negative effects of various agents used in "therapy." Thus, as shown in Example 4 hereinbelow, transplantation patients who had undergone chemotherapy or radiation therapy and who have been administered prednisone and/or cyclosporin A as immunosuppressive agents are benefitted by coadministration of pentoxifylline (PTX) and the P450 inhibitor quinolone ciprofloxacin (CIPRO).

THE INVENTION ASSAY

The compounds of Formula I are shown to modulate the effects of primary stimuli which elevate levels of the relevant subspecies of PA and DAG using the assay system of the invention. In general for the assay, the cells to be tested are first incubated with the primary stimulating agent for various time periods and fixed in ice-cold methanol. The lipids are extracted using, for example, chloroform:methanol 2:1 (v/v), and the extracts are then subjected to HPLC as described by Bursten and Harris, *Biochemistry* (1991). In this method, a Rainin mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. Thus, the relevant peaks of unsaturated PA and DAG are shown in the elution pattern. It is important to note that the assay method permits discrimination between various forms of PA and DAG so that those relevant to the pathway affected by the compounds of Formula I can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

Although the foregoing outline of the invention assay is presented with respect to use of suitable target cells, subcellular units may also be used as substrates for the assay. Included among such subcellular entities are microsomes derived from mesenchymal and/or ectodermal cells, particularly microsomes from marrow stromal cells or human or rat mesangial cells; microsomes or synaptosomes derived from bovine brain; plasma membrane-enriched microsomes or plasma membranes derived as described in Bursten et al., *J Biol Chem* (1991) 226:20732–20743, incorporated herein by reference; detergent-solubilized microsomes; synaptosomes, and membranes or other cell preparations solubilized using, for example, NP-40, Miranal, SDS or other neutral detergents; and detergent-solubilized or further purified preparations of cell proteins, including the proteins LPAAT and/or PAPH.

To test the effect of the compounds of the invention, the candidate compound is included in the initial incubation at various concentrations. Fixing, extraction and HPLC are conducted as above. The effect of the candidate compound is then reflected in a lowering of the relevant PA and DAG levels as compared to the cells without candidate in the control as illustrated hereinbelow.

As stated above, although the effect of coadministering an inhibitor of P450 in vivo is believed to be inhibition of the xanthine metabolic pathway, presumably not relevant to the foregoing in vitro assay method, corresponding compounds appear to have a similar effect in vitro as verified in Example 2 hereinbelow. Accordingly, the foregoing method based on lipid extraction followed by HPLC may also be employed to screen compounds expected to have a corresponding in vivo effect when administered with the compounds of Formula I. In such screening assays, the incubation with primary stimulus is conducted in the presence of the compound of Formula I and in the presence and absence of the candidate "helper" compound.

In an additional assay method of the invention, the effect of coadministering a xanthine compound with a candidate inhibitor for P450 can be assessed using transformed NIH3T3-D5C3 cells and comparing the effect on transformation phenotype among control, incubation with the xanthine derivative alone, and coincubation of the xanthine derivative with the P450 enzyme inhibitor.

COMPOUNDS FOR USE IN THE INVENTION

The compounds of the invention are of the formula

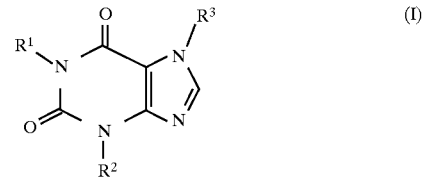

wherein one and only one of $R^1$ and $R^3$ is a straight-chain or branched-chain ω- or (ω-1)-hydroxyalkyl(5–8C), or is an (ω-1)-oxoalkyl (58C) or is an (ω,ω-1) or (ω-1,ω-2)-dihydroxyalkyl (5–8C), or is an alkenyl substituent (5–8C), and the other is alkyl (1–12C) optionally containing one or two non-adjacent oxygen atoms in place of C, and wherein $R^2$ is alkyl(1–12C) optionally containing one or two non-adjacent oxygen atoms in place of C.

These compounds are prepared as described in the above-cited references, including U.S. Pat. No. 3,737,433, Belgium Patent 831,051, and PCT Application EP 86/00401, filed 8 Jul. 1986.

As used herein, straight- or branched-chain alkyl refers to a saturated hydrocarbyl substituent of the specified number of carbons, such as, for alkyl (1–12C), methyl, ethyl, isopropyl, t-butyl, n-hexyl, i-hexyl, n-decyl, 2-methylhexyl, 5-methyloctyl, and the like. ω or ω-1-hydroxyalkyl(5–8C) refers to straight-chain or branched-chain alkyl groups of 5–8 carbons containing a hydroxyl group at the ω or ω-1 position, such as 5-hydroxypentyl, 5-hydroxyhexyl, 6-hydroxyhexyl, 6-hydroxyheptyl, 5-hydroxy-5-methylhexyl, 5-hydroxy-4-methylhexyl, and the like. Similarly, an ω-1-oxoalkyl(5–8C) refers to, for example, 4-oxopentyl, 5-oxohexyl, 6-oxoheptyl, 5-methyl-6-oxoheptyl, and the like.

The compounds of the invention may also include substituents which are alkyl groups optionally containing one or two nonadjacent oxygen atoms in place of carbon. Thus, these substituents include, for example, methoxyethyl, ethoxypropyl, 2'-hydroxyethoxypropyl, and the like.

Particularly preferred compounds for use in the invention include those wherein $R^1$ is a straight chain or branched chain ω- or (ω-1)-hydroxyalkyl(5-8C), or is an (ω-1)-oxoalkyl(5–8C) and $R^2$ and $R^3$ is each independently an alkyl(1–12C) optionally containing one or two non-adjacent oxygen atoms in place of C. Particularly preferred are those compounds wherein $R^1$ is (ω-1)-hydroxyalkyl or (ω-1)-oxoalkyl. Preferred embodiments for $R^2$ include lower alkyl (1–4C), especially methyl and ethyl. Preferred embodiments for $R^3$ include alkyl(1–6C) optionally containing 1 or 2 non-adjacent oxygen atoms in place of C. Particularly preferred embodiments of $R^3$ include methyl, ethyl, n-propyl, 2-ethoxyethyl, 2-methoxyethoxymethyl, ethoxymethyl and n-butyl. Also particularly preferred are compounds of Formula I wherein $R^1$ is 4-oxopentyl, 4-hydroxypentyl, 5-oxohexyl, 5-hydroxyhexyl, 6-oxoheptyl or 6-hydroxyheptyl. Especially preferred are those embodiments wherein the compound of Formula I is 1-(5-hydroxyhexyl)-3,7-dimethylxanthine, 1-(5-oxohexyl)-3,7-dimethylxanthine or 1-(5-methyl-5-hydroxyhexyl)-3,7-dimethylxanthine.

Another group of compounds useful in the invention methods is of the formula

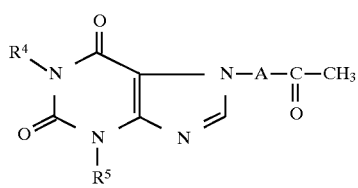

(II)

in which $R_4$ and $R_5$ are the same or different and are selected from the group consisting of straight-chain or branched alkyl radicals with 2 to 6 carbon atoms, cyclohexyl, alkoxyalkyl and hydroxyalkyl radicals, and A represents a hydrocarbon radical with up to 4 carbon atoms which can be substituted by a methyl group.

The following metabolites of pentoxifylline are also useful: Metabolite I, 1-(5-hydroxyhexyl)-3,7-dimethylxanthine; Metabolite II, 1-(5,6-dihydroxyhexyl)-3,7-dimethylxanthine; Metabolite III, 1-(4,5-dihydroxyhexyl)-3,7-dimethylxanthine; M-4-ie-1-(4-carboxybutyl)-3,7-dimethylxanthine; M-5:1-(3-carboxypropyl)-3,7-dimethylxanthine, M-6:1-(5-oxohexyl)-3-methylxanthine; and M-7:1-(5-hydroxyhexyl)-3-methylxanthine.

USES OF THE INVENTION COMPOUNDS AND PHARMACEUTICAL FORMULATIONS

The compounds of Formula I, as shown hereinbelow, provide a mechanism to maintain homeostasis in cells contacted by primary stimuli through mitigating the effects of these primary stimuli on the secondary signaling pathways invoked within seconds of the primary stimulus.

The stimuli referred to herein are of wide variety and include, for example a variety of cytokines, growth factors, oncogene products, putatively therapeutic agents, irradiation, viral infection, toxins, bacterial infection and the products thereof, and the like. Any stimulus which, if not counteracted, has a deleterious effect on the target cell is included within the definition.

For example, the compounds of Formula I are used in connection with patients undergoing bone marrow transplantation (BMT), regardless of whether the BMT is matched allogeneic, mismatched allogeneic, or autologous. Patients receiving autologous transplants are aided by treatment with compounds of Formula I even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient.

In general, chemotherapy and radiation are delivered to the patient for 7–10 consecutive days before the patient gets the new or stored bone marrow infused. The day on which the marrow is given to the patient is referred to as day 0 of the transplant; previous days on which the patient received chemo/radiation are designated by negative numbers. Subsequent days are referred to by positive numerals.

The median time in which negative responses occur in BMT recipients occurs within the first 100 days after transplant. Therefore, statistically, once patients survive the day 100, their chances for continued survival are significantly enhanced. As shown in the examples hereinbelow, compounds of Formula I are able to increase the percentage of patients who survive. The percentage of fatalities within the first 100 days considered acceptable is 15–20% for "good risk" patients and 30–40% for "high risk". These fatalities are due to the direct effects of high doses of chemo/radiation; in addition, GVHD contributes to the death rate in allogeneic marrow recipients.

As illustrated hereinbelow, administration of pentoxifylline along with a quinolone thought to repress xanthine metabolism by inhibiting P450 has a positive effect on these transplant recipients, regardless of the bone marrow source.

Other suitable subjects for the administration of compounds of Formula I, with or without a P450 inhibitor, include patients being administered toxic agents for the treatment of tumors, such as chemotherapeutic agents or irradiation therapy, as well as treatment with biological response modifies such as IL-2 and tumor suppressing cells such as lymphokine activated killer cells (LAK) and tumor-infiltrating lymphocytes (TIL cells); patients suffering from neoplasias generally, whether or not otherwise treated, including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as shown patients undergoing cardiac surgery; patients who are afflicted with autoimmune diseases, thus requiring deactivation of T and B cells, and patients who have neurological disorders.

In general, the effect of the compounds of Formula I in vivo may be enhanced by addition of compounds that inhibit the xanthine-derivative metabolic and clearance pathways, especially those that inhibit P-450. In addition to the quinolone ciprofloxacin illustrated hereinbelow, other suitable agents (mg range daily dosage) include: propranolol (20–100), metaprolol (20–100); verapamil (100–400), diltiazem (100–400), nifedipine (60–100); cimetidine (400–2, 400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); and mexiletine (100–1, 000).

For combination therapy, the compounds of Formula I and the P450 inhibitors can be administered individually or in a single composition. The suitable formulation will depend on the nature of the disorder to be treated, the nature of the medicament chosen, and the judgment of the attending physician. In general, these compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The compounds of the invention can be formulated and administered as free bases or in the form of their pharmaceutically acceptable salts for purposes of stability, convenience of crystallization, increased solubility, and the like.

The amount of xanthine in such compositions is such that a suitable dosage will be obtained. Preferred compositions and preparations according to the present invention are prepared so that an oral dosage unit form contains between about 1.0 mg and about 600 mg of active compound.

While dosage values will vary, good results are achieved when the xanthines of Formula I are administered to a subject requiring such treatment as an effective oral, parenteral, or intravenous sublethal dose of about 1,200 to about 3,200 mg per day. A particularly preferred regimen for use in leukemia is 4 mg/kg body weight, or 300 mg infused over 20–30 minutes 5–6 times daily for 21 days. It is to be understood, however, that for any particular subject, specific dosage regimens should be adjusted to the individual's need and to the professional judgment of the person administering or supervising the administration of the xanthines; the dosages set forth herein are exemplary only and do not limit the scope or practice of the invention.

Depending on the compound of Formula I selected, the level of dosage can be appreciably diminished by coadministration of a P450 inhibitor such as the quinolone illustrated below. Many P450 inhibitors and compounds of Formula I are compatible and can be formulated in a combined dosage. However, the compounds can also be coadministered separately.

The following examples are intended to illustrate but not to limit the invention.

EXAMPLE 1

Effect of Pentoxifylline on Mesangial Cell Activation

This example shows that pentoxifylline inhibits two enzymes in the phospholipid secondary messenger pathway: lyso-PA acyl transferase (LPAAT) and phosphatidic acid phosphohydrolase (PAPH). This is demonstrated using the assay method of the invention by showing that concentrations greater than 500 µM pentoxifylline obviate the elevation in levels of unsaturated, non-arachidonic PA and of the DAG derived from it that result from stimulation of the cells with IL-1. This example also illustrates the method of the invention.

Human glomerular mesangial cells were incubated with IL-1 for various time periods of 5–60 seconds and the cells were fixed in ice-cold methanol, and the lipids extracted using chloroform:methanol 2:1 (v/v). It is very important that the fixing/extraction process be conducted quickly so that the decomposition of unstable intermediates is halted.

The extracts were subjected to HPLC on a Rainin mu-Porasil column with a 3:4 hexane:propanol organic carrier and a 1–10% water gradient during the first 10 minutes of separation. The relative concentration of each lipid species is determined using absorption at 206 nm ($A_{206}$), which follows unsaturated acyl content of lipid species. However, it has been shown that the unsaturated PA and DAG acyl groups do not include arachidonates. The absolute mass of each lipid species is determined by isolation of the lipid using a fraction collector, repurification on the HPLC column. Determination of phospholipid phosphorus is as nmoles/mg cellular protein. Protein concentration is determined using the Bradford technique.

The results for control human mesangial cells lipids are shown in FIG. 1. Abbreviations used in FIGS. 1–11 are: DAG, diacylglycerol; chol. esters, cholesterol esters; PA, phosphatidic acid; lyso-PA, lysophosphatidic acid; PE, phosphatidyl ethanolamine; Pi, phosphatidyl inositol; PS, phosphatidylserine; and PC, phosphatidyl choline.

The distribution of lipid metabolites seen in FIG. 1 is constant within 2% for human glomerular mesangial cells (HMC) maintained in culture under controlled situations. The low levels of PA, lyso-PA and DAG (as compared to PE) may be noted.

Figure 3:
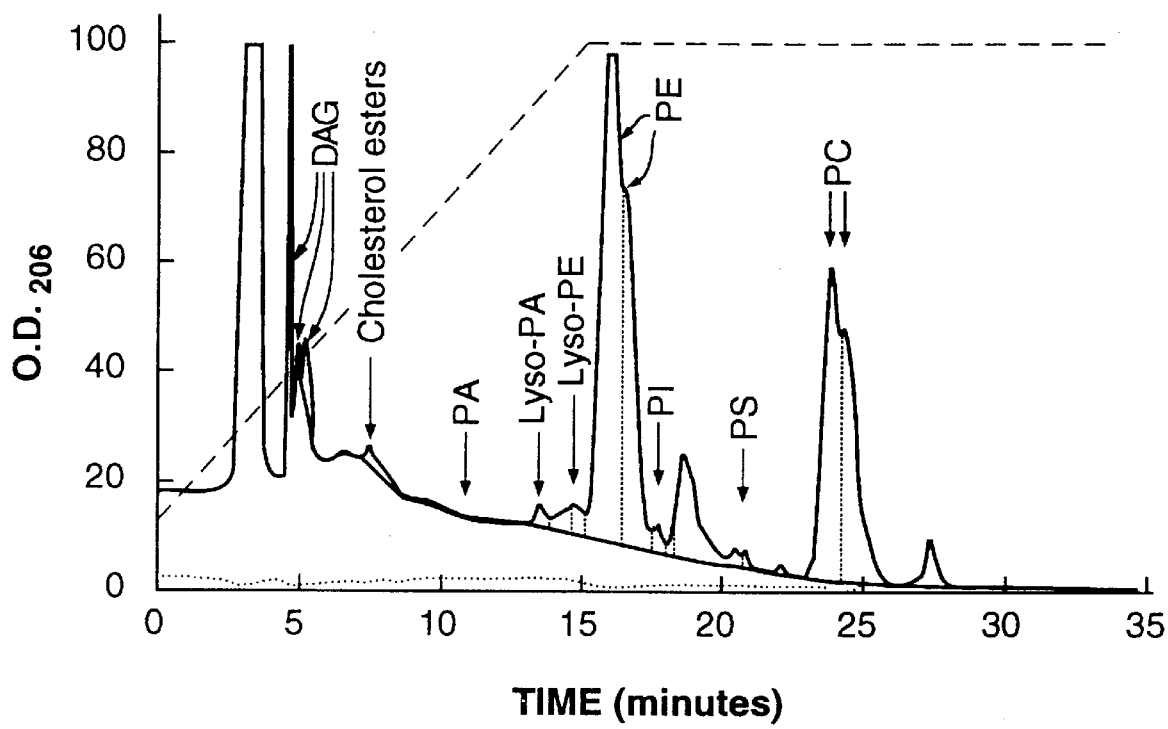
Figure 4:
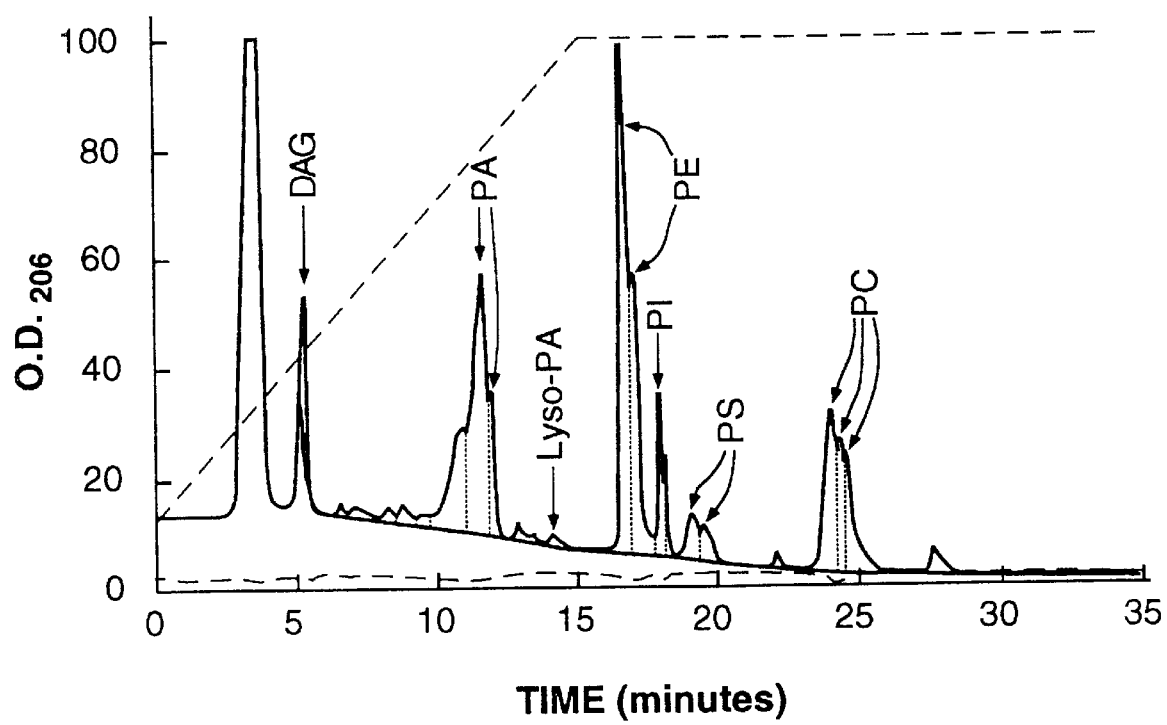

After contacting HMC with $10^{-11}$M interleukin-1, a marked redistribution of phospholipids and metabolites is apparent within 5 seconds (FIG. 2), including a significant increase in PA and DAG. FIGS. 3 and 4 show the HPLC after stimulation with IL-1 for 15 seconds and 60 seconds, respectively. PA has been converted into DAG by action of phosphatidate phosphohydrolase at 15 seconds; but the PA peak reappears after 60 seconds.

To verify that this reappearance of PA is not due to resynthesis from DAG, HMC were incubated with the diacylglycerol kinase inhibitor R 50922 that prevents phosphorylation of DAG to PA. This does not alter the HPLC pattern obtained. To confirm this finding, fast-atom bombardment mass spectrometry of the PA and DAG fractions was performed, illustrating that the predominant PA species formed were 1-oleoyl (C18:1) 2-linoleoyl (C18:2), and 1-linoleoyl 2-linoleoyl PAs (m/z ratios respectively 699 and 697), which where then converted into 1-oleoyl, 2-linoleoyl and 1,2-Sn-dilinoleoyl diacylglycerols (m/z ratios respectively 618–620 and 616–618, the spread in m/z values due to differential protonation prior to fast-atom bombardment).

Figure 5:
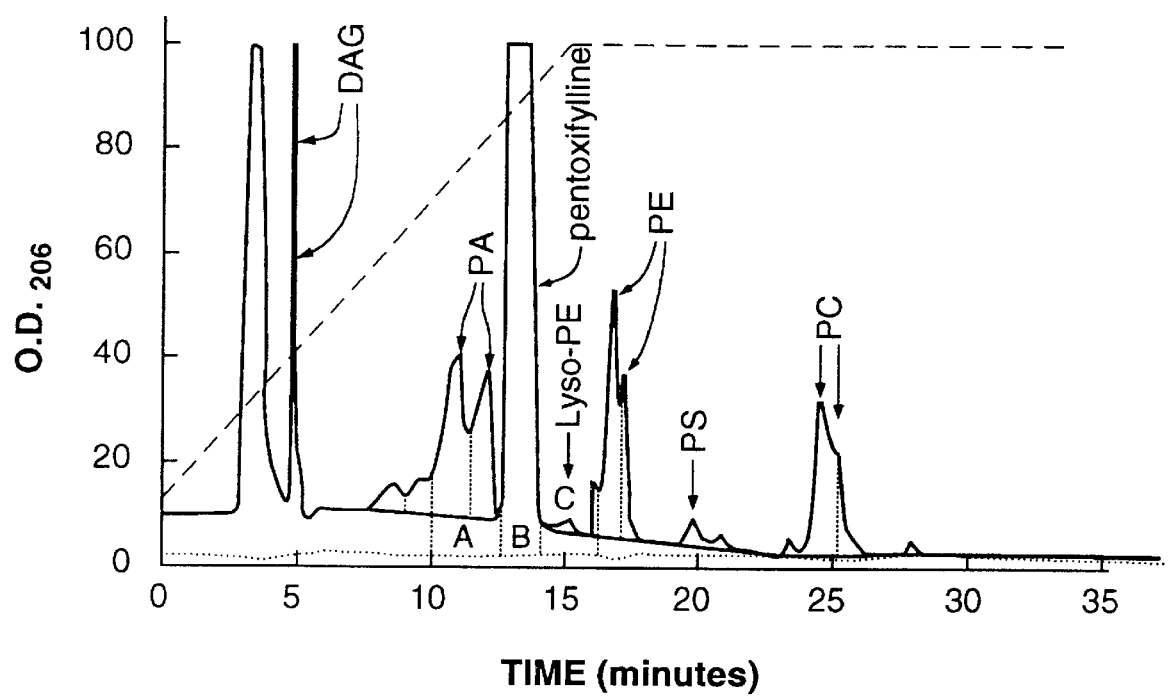
Figure 6:
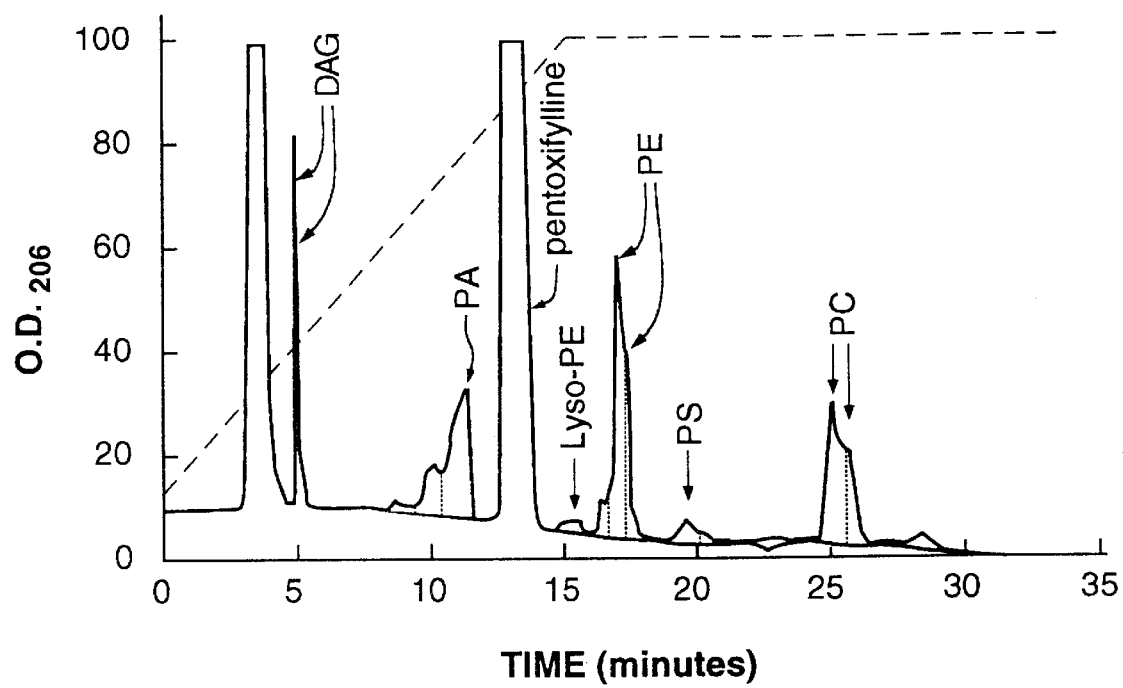

The HMC were also reacted with $10^{-11}$M IL-1 in the presence of various concentrations of pentoxifylline. At 100 µM pentoxifylline, there was no change of human mesangial cell cyclical formation of PA, and conversion of PA to DAG as seen at 15- and 60-second points. These results are shown in FIGS. 5 and 6 which show the HPLC after 15 seconds and 60 seconds, respectively, of incubation with IL-1 in the presence of 100 µM pentoxifylline. A large peak representing pentoxifylline is present.

Figure 7:
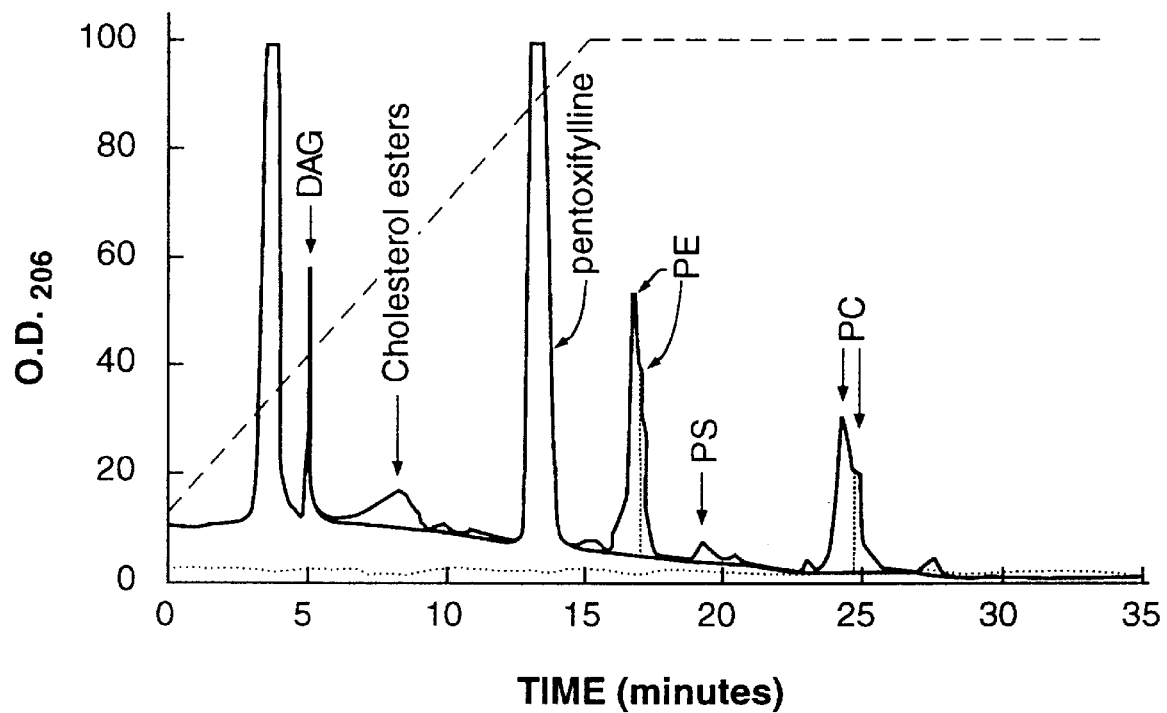

At 500 µM, pentoxifylline results in a slight attenuation in the conversion of PA to DAG, but does not abolish the response, as shown in FIG. 7, which represents a 15 second time point.

PTX at 1 mM abolishes the elevation of PA and DAG by IL-1 at all time points examined after IL-1 stimulation. FIGS. 8–11 show the HPLC of mesangial cell lipids following stimulation of HMC with IL-1 for various times in the presence of 1 mM pentoxifylline.

Figure 8:
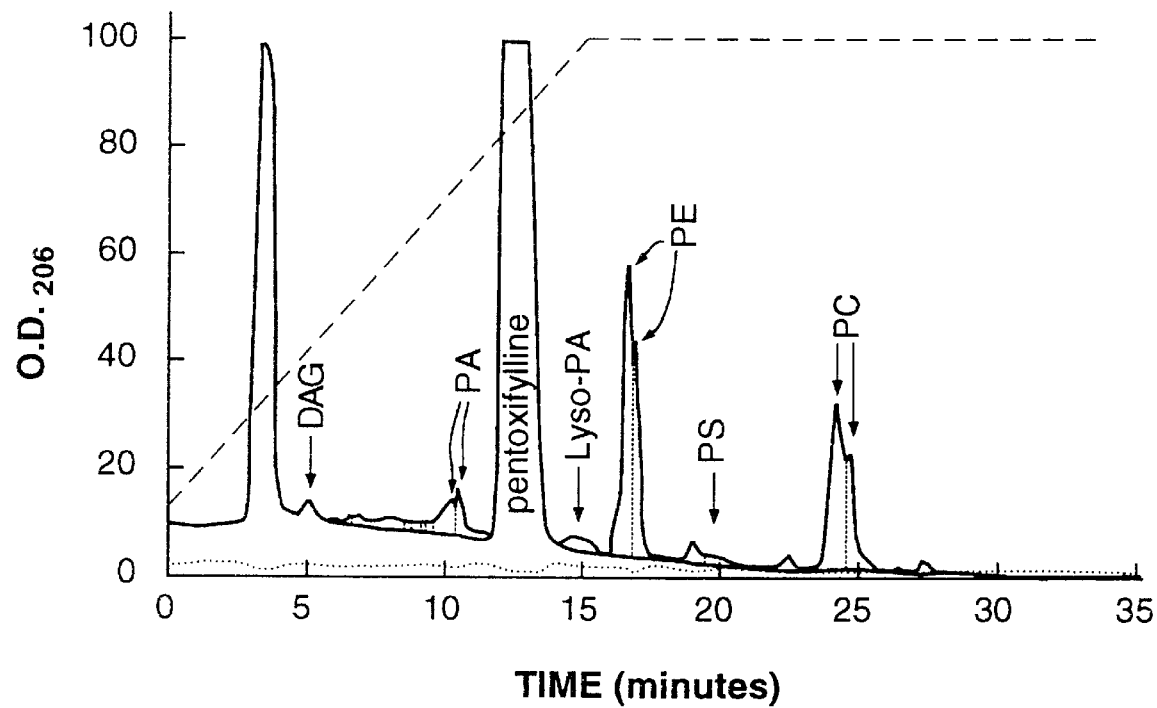
Figure 9:
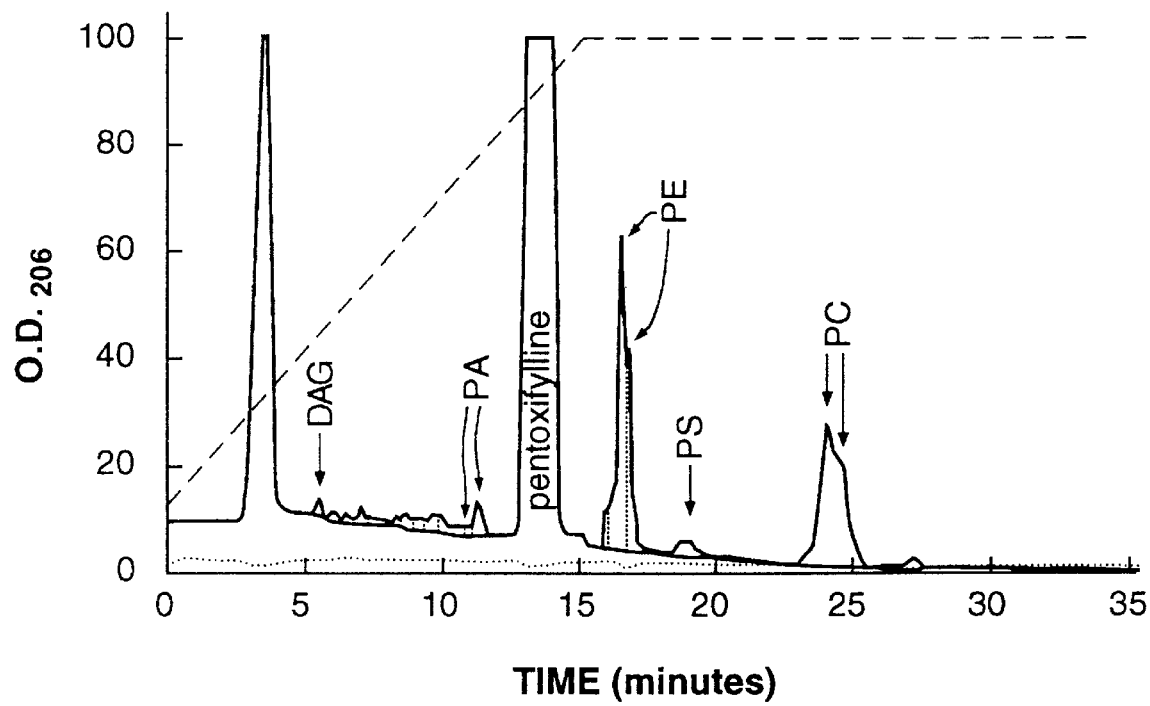
Figure 10:
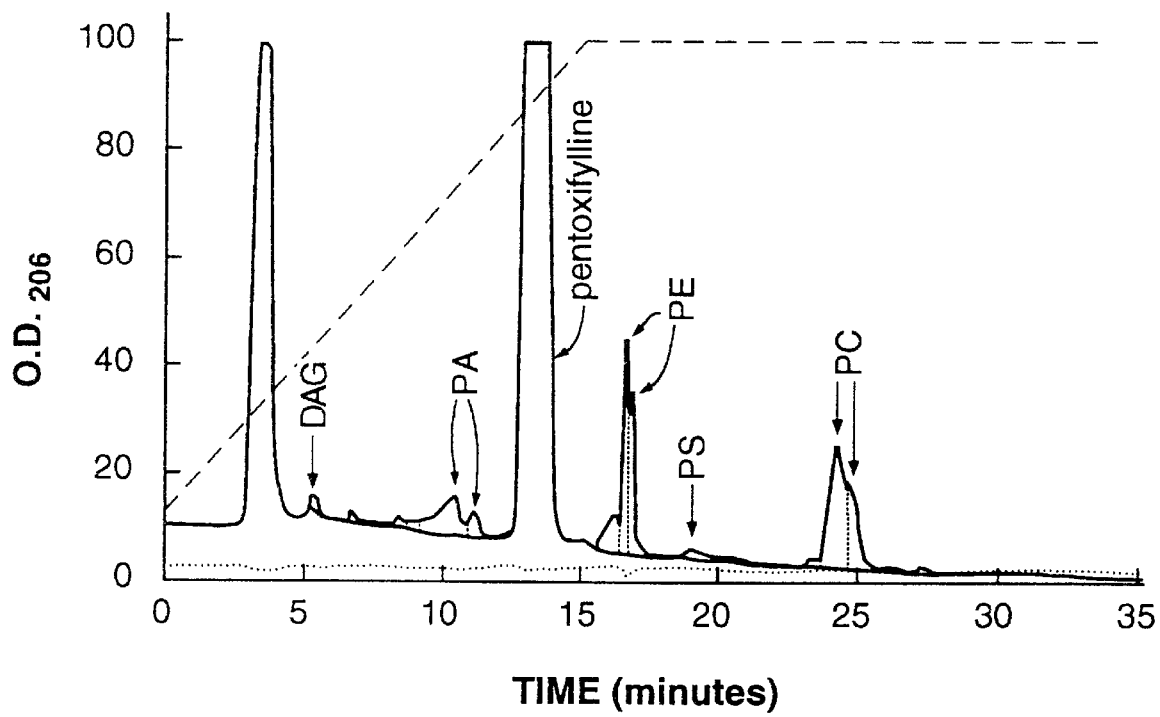
Figure 11:
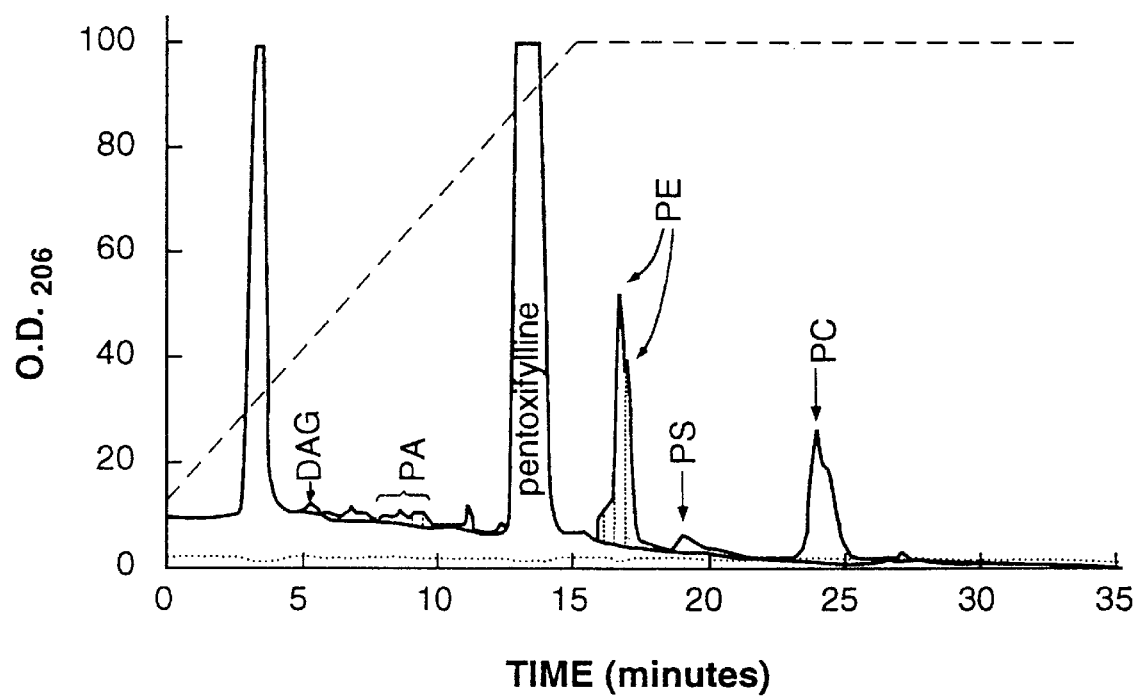

FIG. 8 shows the HPLC after 15 seconds.
FIG. 9 shows the HPLC after 30 seconds.
FIG. 10 shows the HPLC after 45 seconds.
FIG. 11 shows the HPLC after 60 seconds.

At all of these time points, the levels of PA and DAG are muted roughly to the level found in unstimulated cells.

Figure 12:
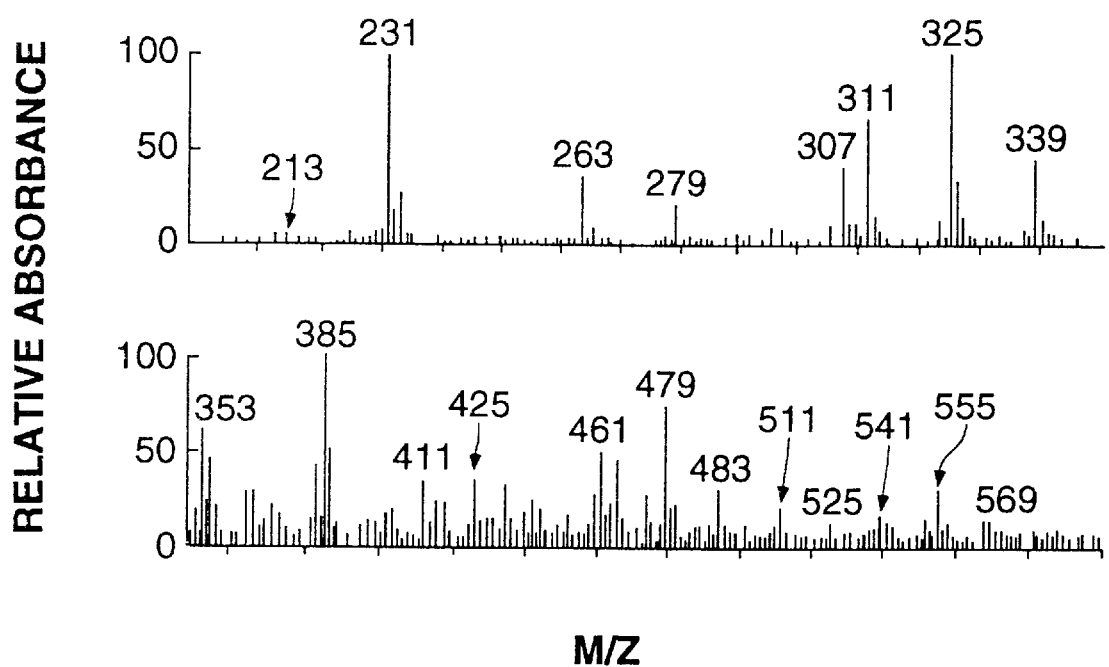
FIG. 12 shows the mass spectrum obtained using fast-atom bombardment of the lyso-PA peak of a typical HPLC trace.

To verify the nature of the various peaks in the HPLC traces shown in FIGS. 8–11 was verified by fast-atom bombardment (FAB) mass spectrometry. Individual components were isolated after separation and analyzed using this technique. The results of analysis of the lyso-PA peak in these traces is shown in FIG. 12. Major peaks appear at 311, 325, 339, 353–357, 381–387, 411, 417, 425, 433, 461, 465, 479, 493 and 555. These represent fatty acyl breakdown products (311, 325, 339) and the primary structures of the following: lyso-phosphatidic acid subspecies including 1-myristoyl lyso PA (381–385), 1-palmitoyl lyso-PA (411), 1-o-2"-ene-linoleoyl lyso-PA (417), 1-linoleoyl lyso-PA (433), 1-C20:1 and 1-C20:2 lyso-PA (461, 465), 1-o-docosanoyl lyso-PA (479), and 1-docosanoyl lyso-PA (493).

Thus, the lyso PA that accumulates contains high levels of unsaturated fatty acids. Pentoxifylline in a dose range greater than 500 µM results in inhibition both of phosphatidate phosphohydrolase and of lyso PA acyl transferase. Subsequent determinations have shown that pentoxifylline at 0.5 mM inhibits PAPH although its inhibitory effect on LPAAT is evident only at higher concentrations.

EXAMPLE 2

The Effects of PTX on Malignant Transformation of Cells

An NIH3T3 cell line (D5C3) provides target cells which were transformed by an activated oncogene. The cells were transformed with a temperature-sensitive v-abl mutant gene. This mutant gene encodes a temperature-sensitive v-abl protein that produces a non-oncogenic product at a non-permissive temperature due to a lack of tyrosine phosphorylation. The cells were incubated at the permissive temperature (33° C.) for 5 days after passage with and without pentoxifylline (1 mM).

Without pentoxifylline, the cells had the typical transformed appearance, growing predominantly as loosely adherent clumps. In the presence of 1 mM pentoxifylline, the overall number of cells was diminished by approximately 50% and they assumed a predominantly non-transformed, fibroblastic appearance, similar to that observed at the non-permissive temperature (39° C.).

Ciprofloxacin at a concentration of 50 μg/ml also has a significant effect. The combination of pentoxifylline (1 mM) and Ciprofloxacin (50 μg/ml) had an additive effect, i.e., greater inhibition of the transformed phenotype than seen with pentoxifylline (1 mM) alone or Ciprofloxacin (50 μg/ml) alone, Table 1.

TABLE 1

Activity of Pentoxifylline and Ciprofloxacin on Blocking Transformed Phenotype of D5C3 Cells

| Treatment | Phenotype* | Growth** |
|---|---|---|
| Control | +++++ | +++++ |
| Pentoxifylline (1 mM) | +++ | +++ |
| Ciprofloxacin (50 μg/ml) | ++ | ++ |
| Ciprofloxacin (50 μg/ml) + Pentoxifylline (1 mM) | + | + |

*The phenotype of the cells was visually graded on a scale of + (1+) to +++++ (5+) where 5+ represents a fully transformed phenotype and 1+ represents a typical fibroblastic appearance of nontransformed NIH3T3 cells.
**The growth of cultured cells was graded from + (1+) to +++++ (5+) where the transformed cells were scored as 5+ (for rapid growth) and the nontransformed cells were scored as 1+ (for slower growth).

Using the method of this example, candidate quinolone type and xanthine compounds can be tested for combined effects, i.e., permitting a lower dosage of xanthine to be used when quinolone is coadministered than if the xanthine were administered alone.

Additionally, NIH3T3 murine fibroblast cells transformed with a mutated K-ras (codon 12 Gly-Val) were tested in vitro and in nude mice. In vitro, without pentoxifylline, the cells grew rapidly, had a typical transformed appearance and formed anchorage-independent colonies in soft agar with high efficiency. Pentoxifylline at concentrations at or greater than 0.5 mM resulted in inhibition of growth and suppression of anchorage-independent growth.

Nude mice were injected subcutaneously with $10^6$ cells and were treated either once or twice daily with 100 mg/kg pentoxifylline intraperitoneally. Control animals treated with only saline injections developed tumors that weighed 2.5±0.2 g after eight days. Animals treated once daily with pentoxifylline had tumors that weighed only 0.45±0.2 g while animals treated twice daily had tumors that weighed 0.2±0.1g.

Similar studies with human-derived tumor cells from breast cancer and rhabdomyosarcoma have shown similar results.

EXAMPLE 3

Effects of Pentoxifylline on Cellular Behavior

SV40 T-antigen-transformed human kidney mesangial cells were cultured under standard conditions with rhIL-1 or with TNFα with and without pentoxifylline (PTX). Transformed mesangial cells grow independently of added growth factors, but IL-1 and TNFα are the normal proliferative signals for mesangial cells. As was shown in Example 1, when IL-1 is added to kidney mesangial cells, within 30 seconds LPAAT and PAPH are activated; the effect of both of these enzymes is inhibited by pentoxifylline at 1 mM. In this experiment, the growth of the treated cells was measured using tritiated thymidine uptake.

Figure 13:
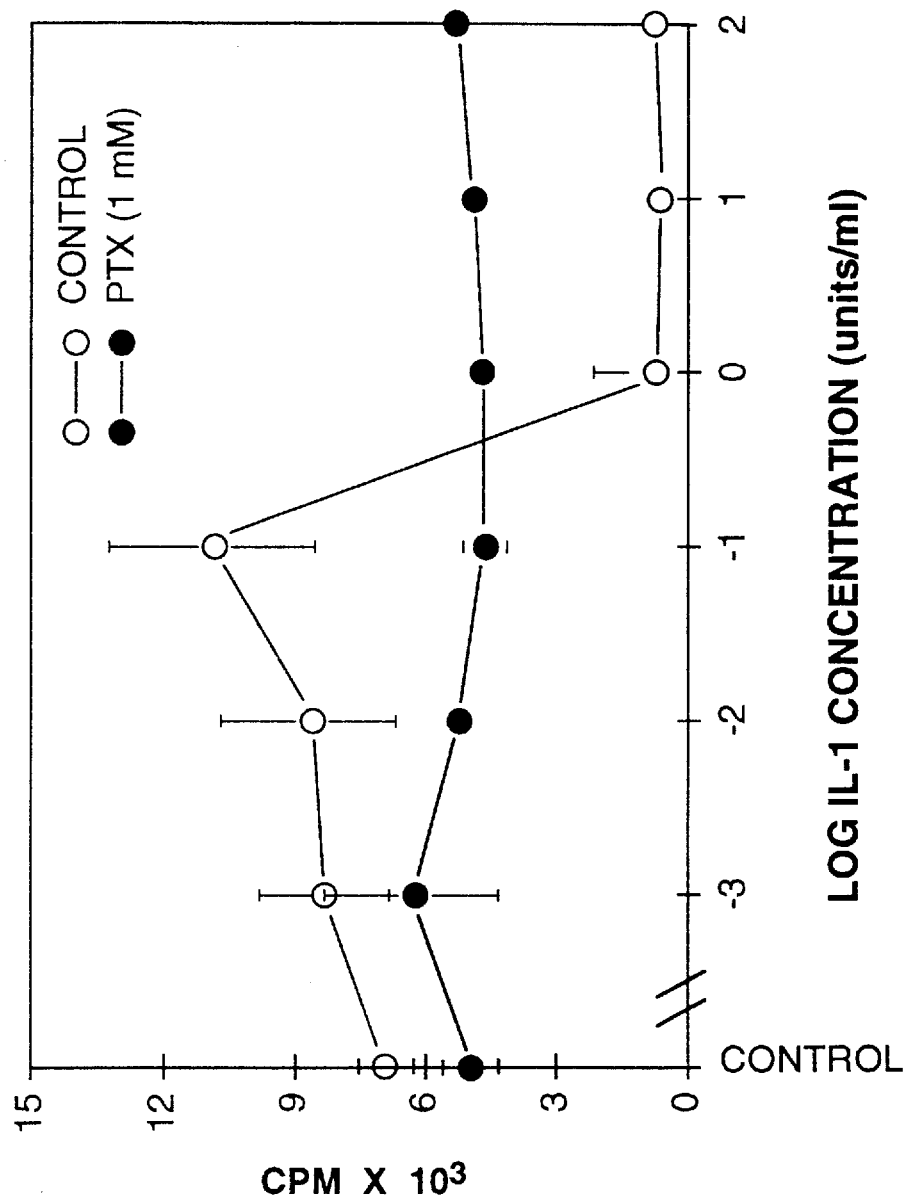
FIGS. 13A and 13B show graphical representation of the effect of pentoxifylline on human mesangial cells stimulated by recombinant human IL-1 (FIG. 13A) and TNFα (FIG. 13B).
Figure 13:
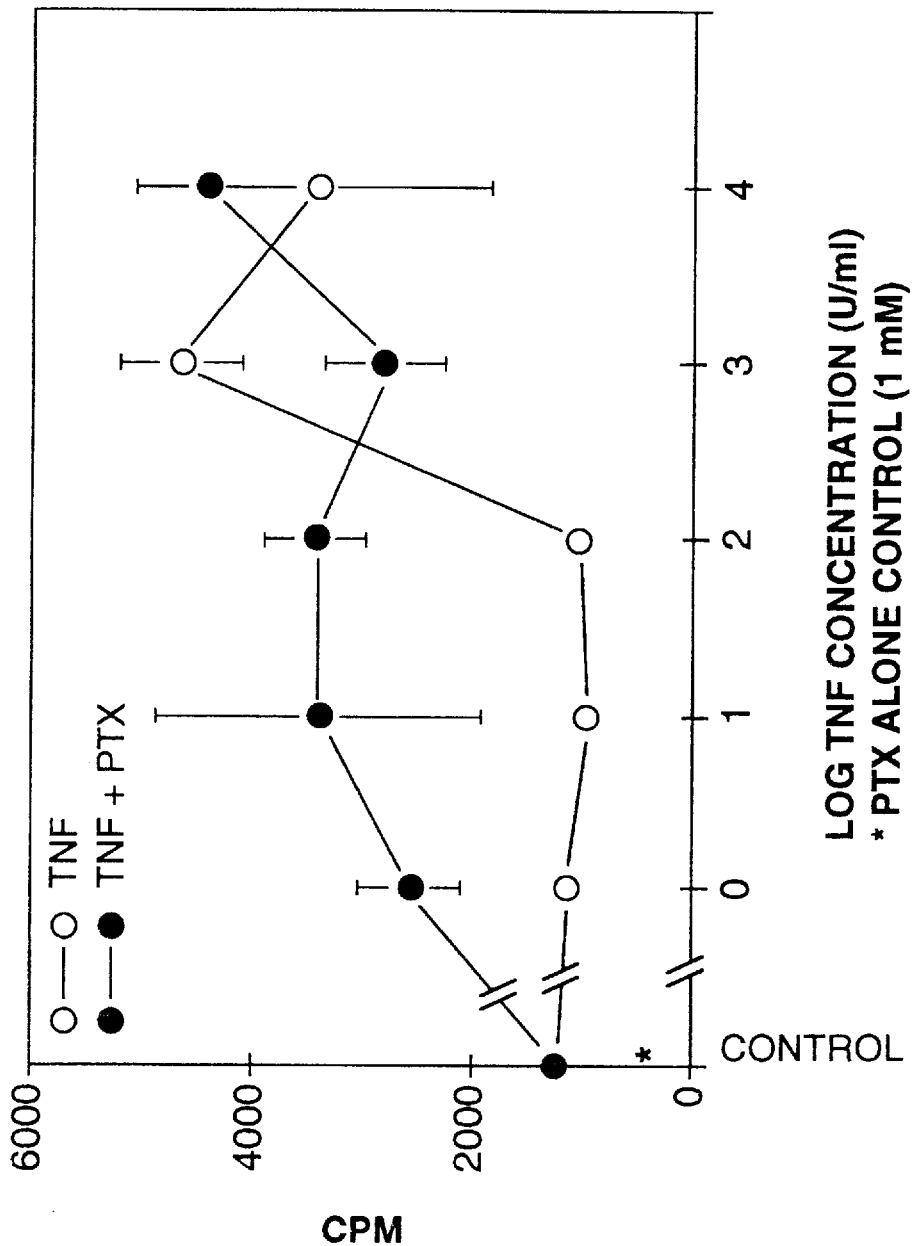

As shown in FIG. 13A, added PTX arrested growth stimulated by IL-1 in the transformed cells, and this could not be reversed by addition of exogenous recombinant human IL-1. FIG. 13B shows that PTX enhances the proliferative effect of TNF in these cells.

Figure 14:
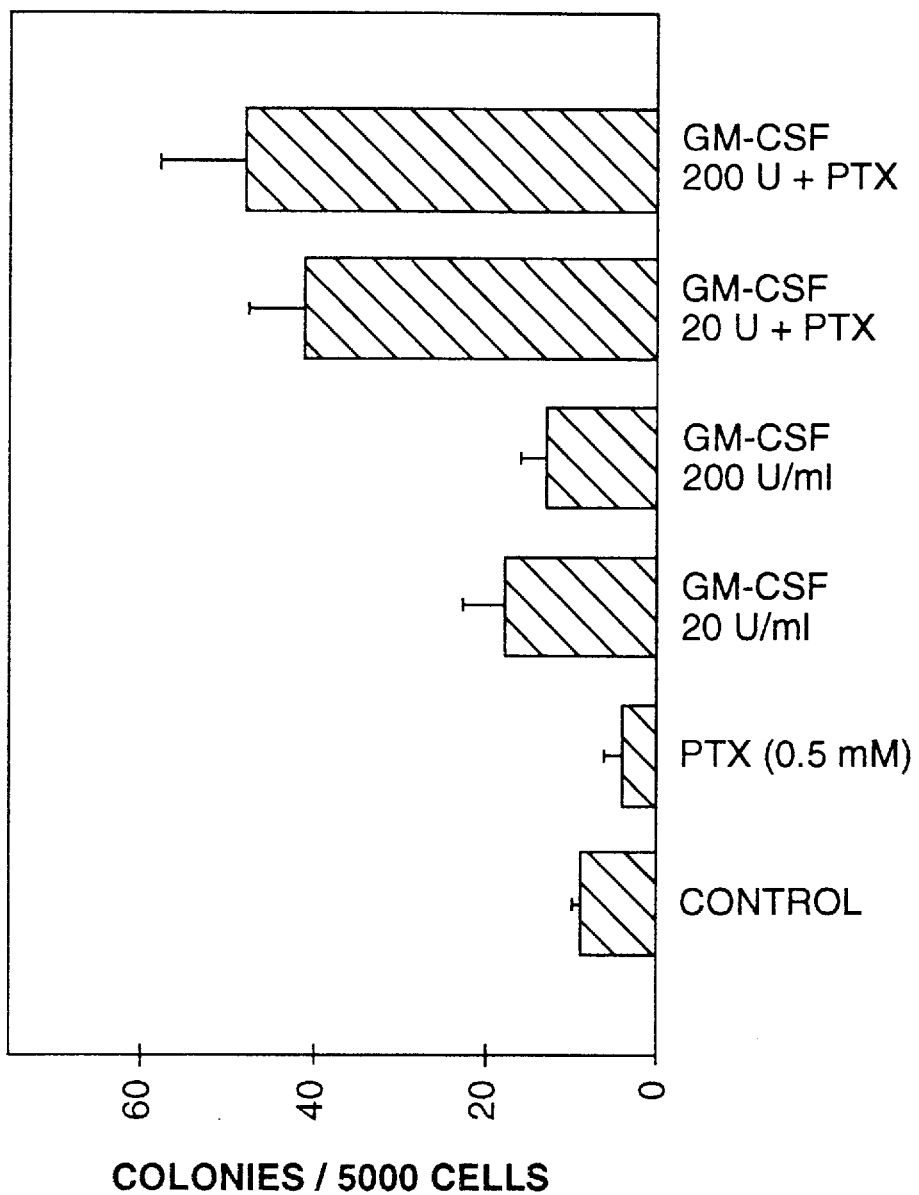
FIG. 14 shows a graphical representation of the effect of pentoxifylline on GM-CSF stimulation of colony formation by the human leukemic cell line MO7e.

The human leukemic cell line (Mo7e) is dependent on added granulocyte-macrophage colony-stimulating factor (GM-CSF) for growth. Mo7e cells were cultured in semi-solid medium with and without pentoxifylline (PTX) and rhGM-CSF. Colonies were counted 10 days after culture initiation under an inverted microscope. As shown in FIG. 14, addition of PTX enhanced GM-CSF-stimulated growth of colonies. PTX thus prevents the up-regulation of activation-associated genes which inhibit proliferation.

Figure 15:
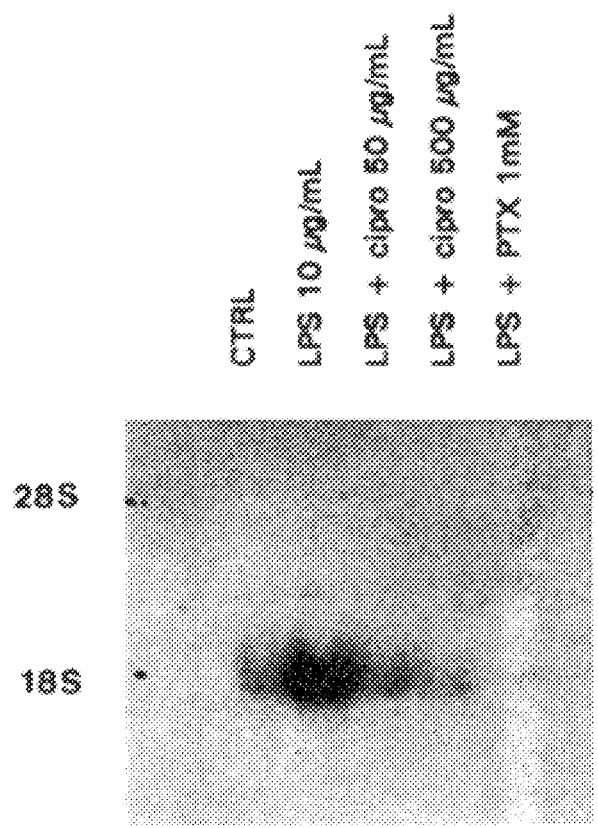
FIG. 15 shows a photocopy of a Northern blot which shows the levels of TNFα transcripts obtained when U937 cells are stimulated with LPS in the absence and presence of pentoxifylline or ciprofloxacin.

The effect of PTX on levels of TNFα transcripts in U937 cells induced with LPS for three hours is shown in FIG. 15. FIG. 15 shows that the addition of 1 mM of PTX enhanced the TNF-stimulated growth of these cells. This figure shows determination of levels of TNF RNA transcripts by Northern blot. As shown, the addition of 1 mM PTX reduces the TNF RNA obtained in response to LPS stimulation to an undetectable level. The quinolone, Ciprofloxacin (CIPRO) has a similar effect, but at lower concentration. These data show that PTX is antiproliferative for certain normal and transformed cells of mesenchymal lineage stimulated by IL-1 and may have growth-arresting properties for certain cancers.

Figure 16:
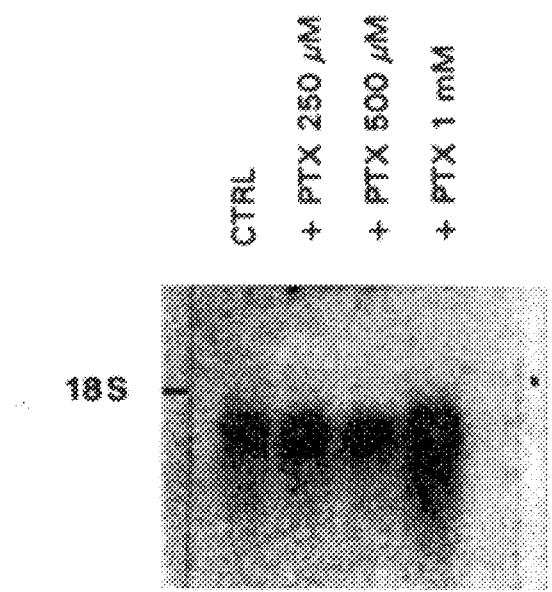
FIG. 16 shows a photocopy of a Northern blot to detect IL-6 transcripts in bone marrow stromal cells in the presence and absence of pentoxifylline.

FIG. 16 shows a Northern blot demonstrating that three-hour exposure of bone marrow stromal cells to increasing concentrations of pentoxifylline (PTX) results in increased production of IL-6 transcripts.

Figure 17:
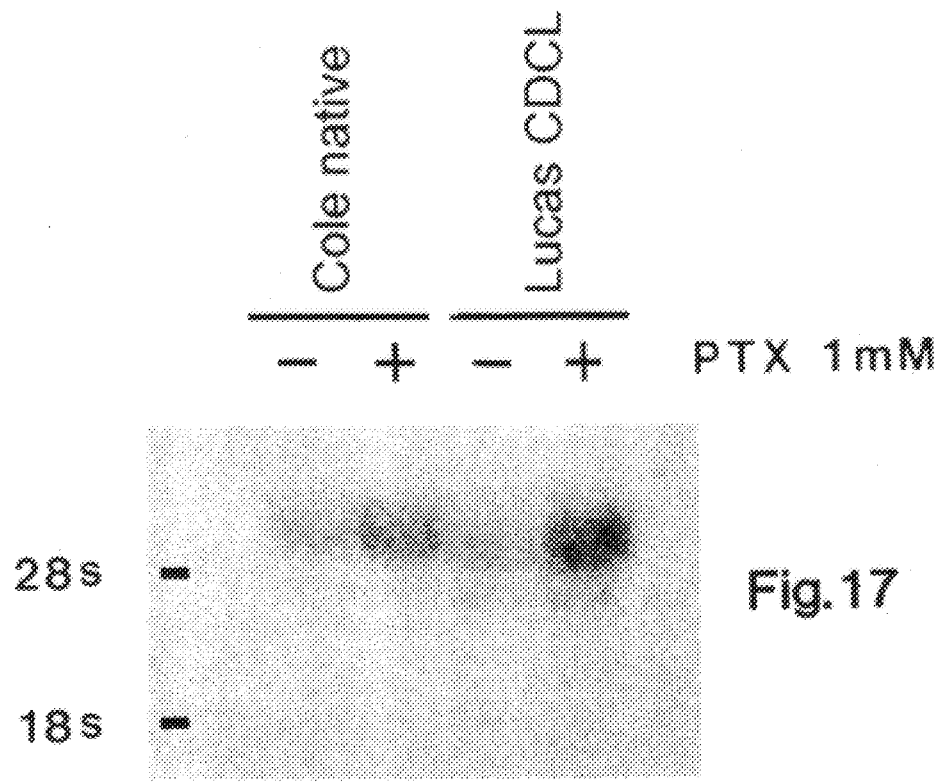
FIG. 17 shows a photocopy of a Northern blot to detect Steel factor transcripts in the presence and absence of pentoxifylline.

The results presented in FIG. 17 show that PTX increases cellular Steel factor cellular activation pathways, i.e., as measured by the levels of Steel factor transcripts after three-hour incubation of passaged (native) or cloned (CDCL) marrow stromal cell lines with PTX (Steel factor has also been termed the c-kit ligand, mast cell growth factor, and stem cell growth factor).

Figure 19A:
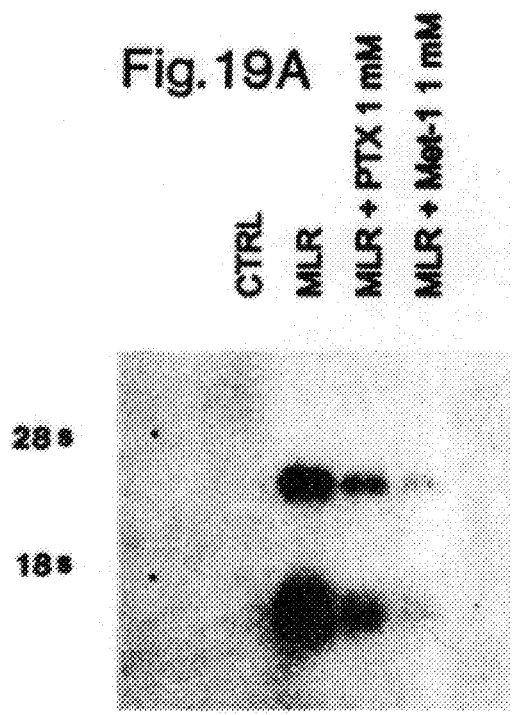
FIGS. 19A, 19B and 19C show photocopies of Northern blots obtained from $CD3^+$ lymphocytes in a mixed lymphocyte reaction with probes for TNF (FIG. 19A), for IL-2 (FIG. 19B) and for IL-2 receptor (FIG. 19C).
Figure 19B:
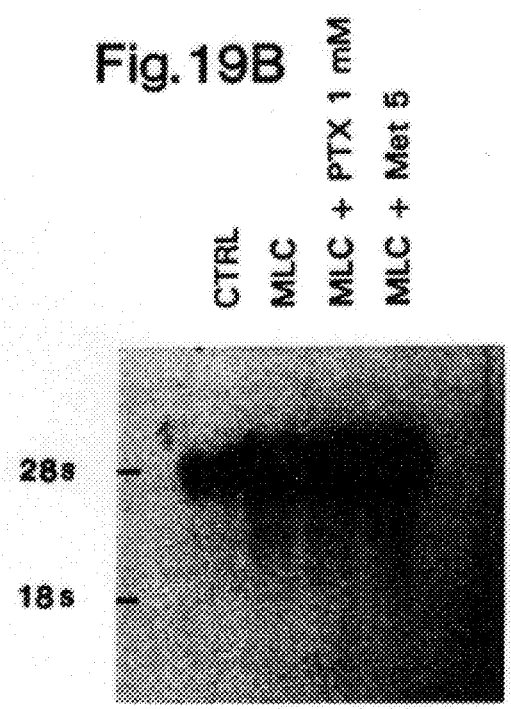
Figure 19C:
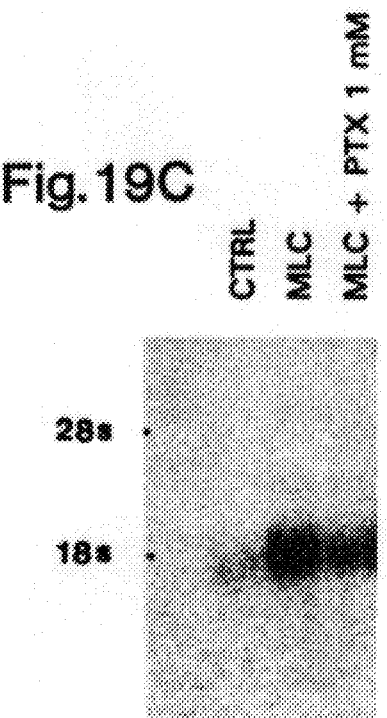
Figure 20:
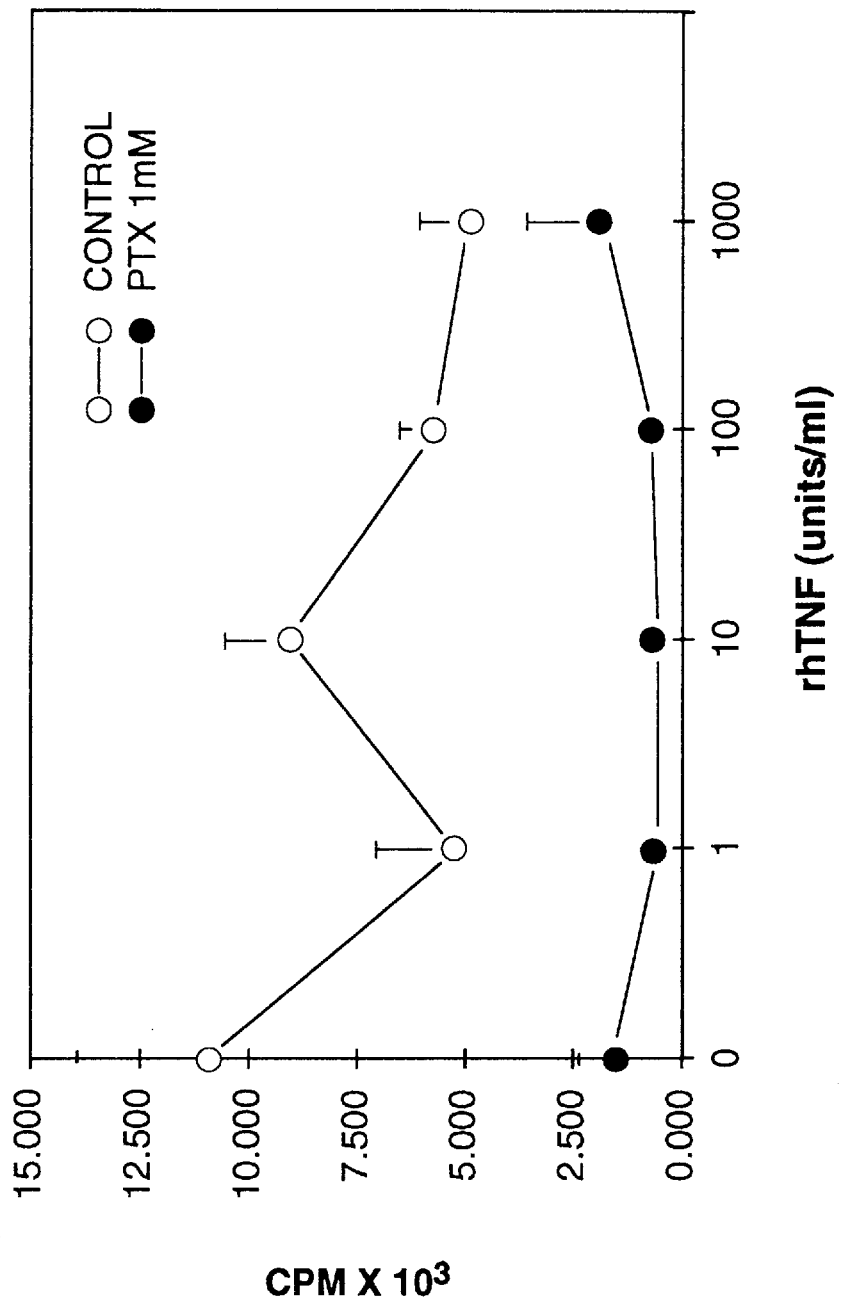
FIG. 20 shows a graphical representation of the effect of TNF on proliferation of $CD_2^+$ cells stimulated by anti-$CD_3$ monoclonal antibody in the presence and absence of pentoxifylline.
Figure 21:
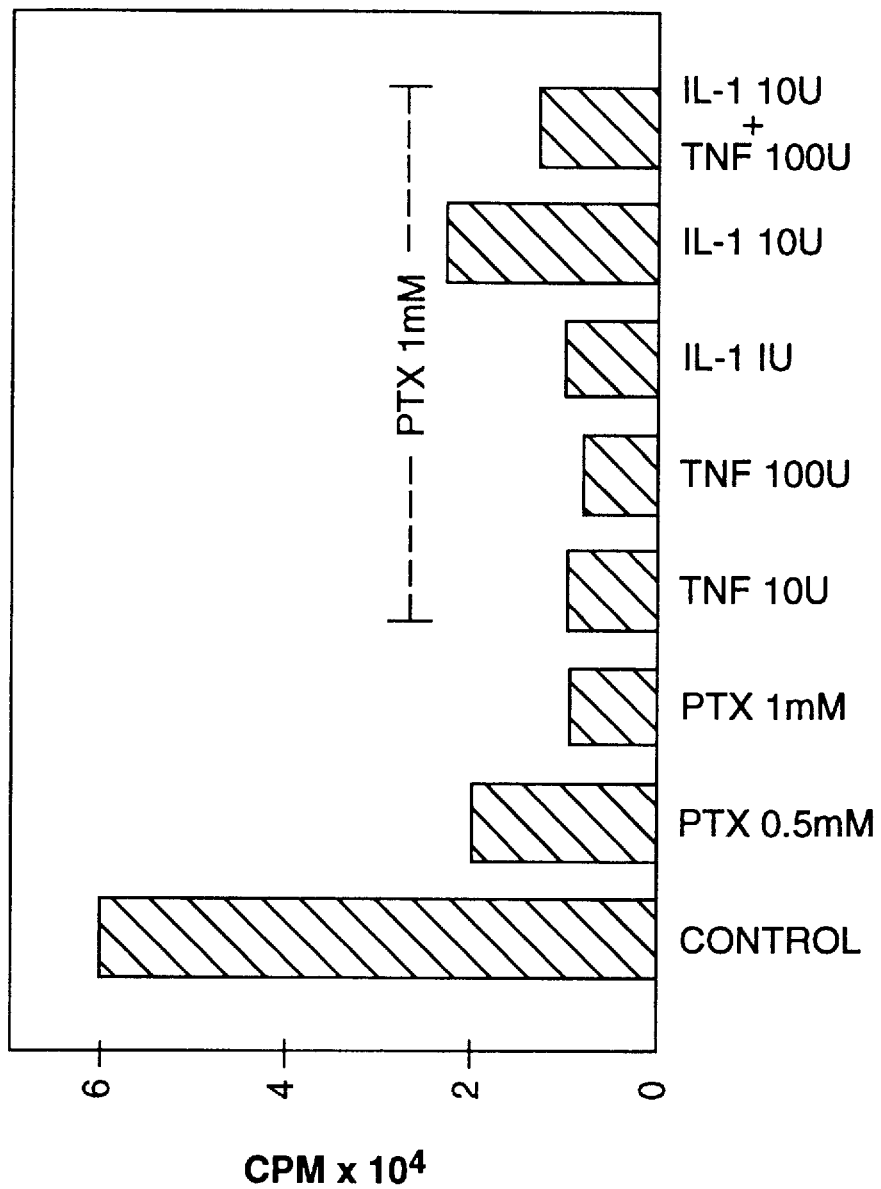
FIG. 21 shows the effect on proliferation of $CD_2^+$ cells stimulated by anti-$CD_3$ antibody in response to various factors in the presence and absence of pentoxifylline.

Proliferation of CD3-positive lymphocytes was strikingly inhibited by PTX. In these experiments, freshly isolated, CD2-positive cells were stimulated by a solid-phase monoclonal antibody to acquire a CD3 phenotype, and then PTX was added. This inhibitory effect on proliferation was accompanied by suppression of TNF and IL-2 receptor transcripts, but not of IL-2 transcripts. FIG. 19 shows the results of probing Northern blots obtained from CD3 positive lymphocytes in a mixed lymphocyte reaction with suitable probes for TNF (FIG. 19A) for IL-2 (FIG. 19B) and for IL-2α receptor (FIG. 19C). The block in proliferation could not be overcome by addition of either tumor necrosis factor (FIGS. 20 and 21) or IL-1 (FIG. 21). FIG. 20 shows that even high concentrations of TNF fail to reverse the inhibitory effect of PTX on thymidine uptake on these cells; FIG. 21 shows the results of a specific experiment wherein CD2-positive T-cells were selected using immunomagnetic beads and stimulated using adsorbed monoclonal antibody 64.1. The cytokines and PTX were added at culture inception and the cells were harvested after 5 days. As shown in these results, thymidine uptake was diminished by PTX in an concentration-dependent manner. The addition of either IL-1 or TNF failed to reverse this inhibition.

Figure 22:
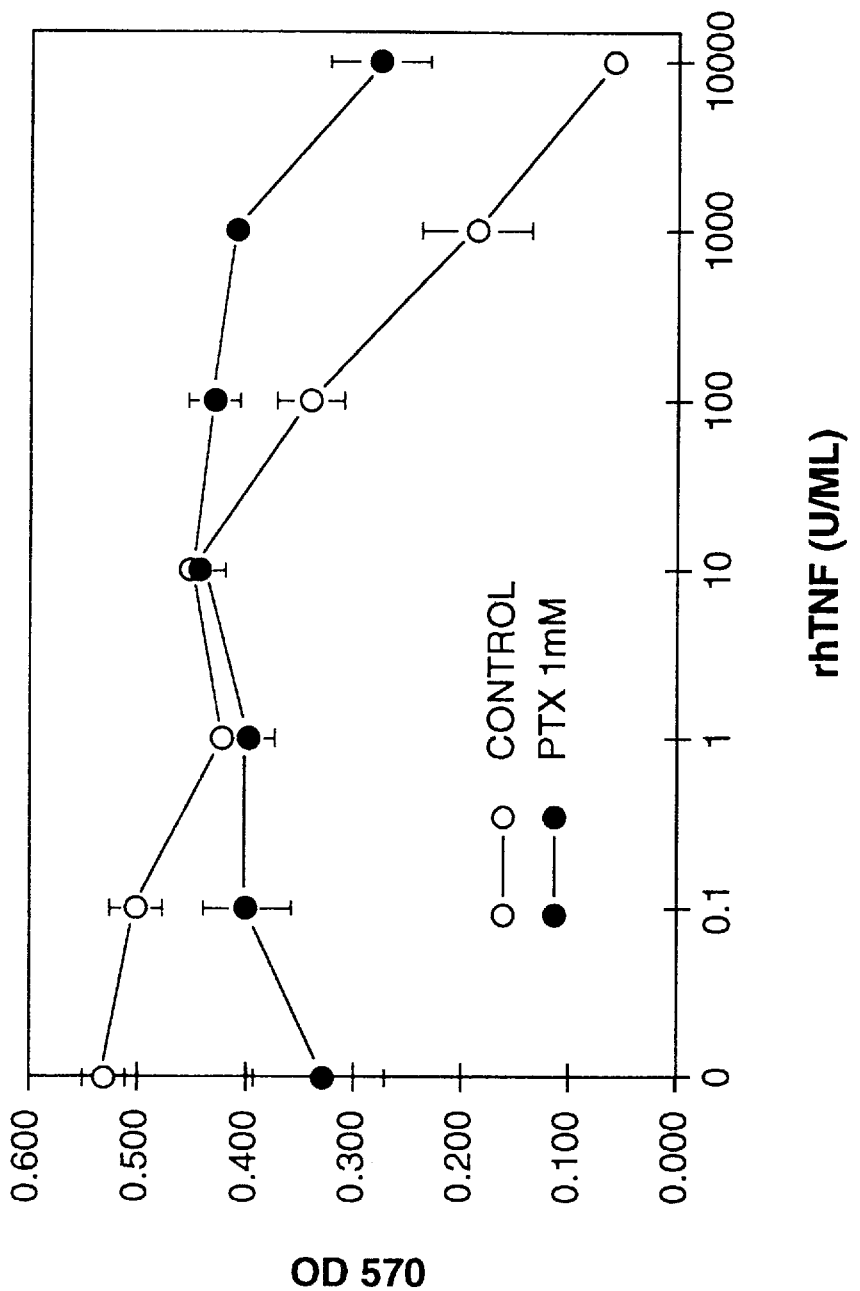
FIG. 22 is a graphical representation of the cytotoxic effect of TNF on murine L929 cells in the presence and absence of pentoxifylline.
Figure 23A:
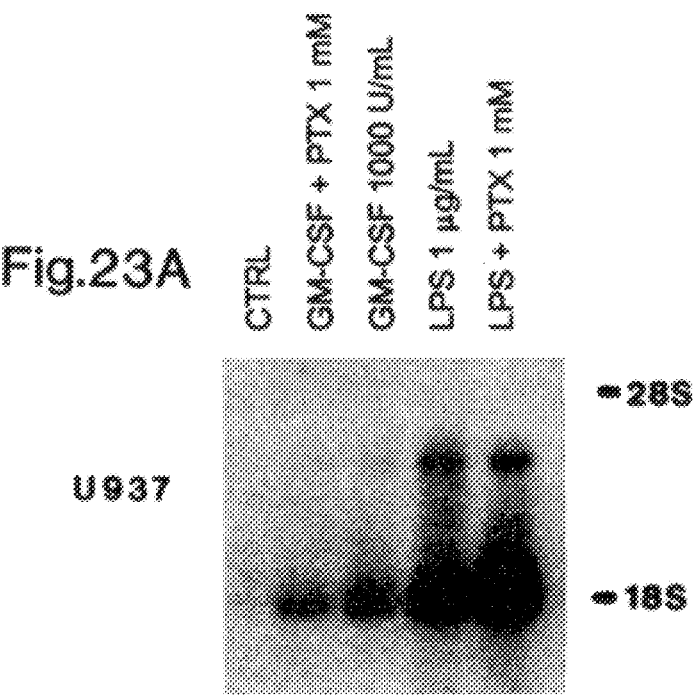
FIGS. 23A and 23B are photocopies of Northern blots showing the effect of various compounds on IL-2 transcript production.
Figure 23B:
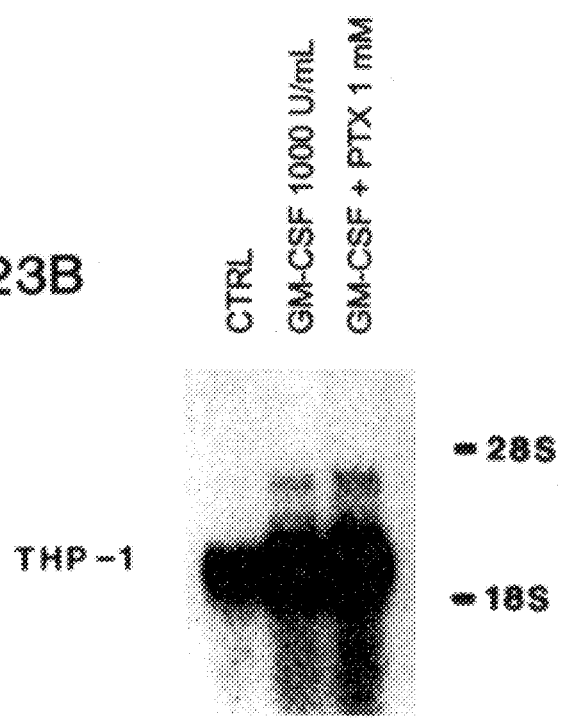

The murine fibrosarcoma cell line, L929, was also tested as an indicator for assays of TNF cytotoxicity. TNF is cytotoxic to these cells in a concentration-dependent manner as shown in FIG. 22. Cell growth was assayed by crystal violet staining using optical density as a measure of growth. Pentoxifylline added at 1 mM concentration, however, is protective against cytotoxicity of TNF. Finally, two monocytic cell lines, U937 and THP1, were used to test the effect of pentoxifylline on the protection of the cytokine IL-8. The cell lines in culture were induced to upregulate IL-8 production by lipopolysaccharide or GM-CSF. Northern blots performed on extracts of these cells and probes for IL-8 encoding mRNA showed that the addition of pentoxifylline did not inhibit, and indeed may upregulate the synthesis of IL-8. Based on the evidence shown in Example 1, it can be concluded that the production of IL-8 is not controlled by a transduction pathway dependent on LPAAT and PAPH.

EXAMPLE 4

Maintenance of Homeostasis

At least one stimulus for complications in bone marrow transplant recipients, even of autologous transplants, includes the irradiation therapy and chemotherapeutic routines imposed on patients undergoing these procedures. Typically, bone marrow transplants in patients bearing tumor burdens are performed in order to restore the non-tumor marrow cells destroyed in the aggressive treatment of the tumor. If the patient's own marrow has been removed and stored for readministration, it is not theoretically necessary to effect immunosuppression since graft-versus-host disease (GVHD) is not a problem. However, if the bone marrow is donated by another person, even if the marrow is matched for histocompatibility, the strong possibility of rejection is present.

Studies were conducted in three types of transplant recipients: patients receiving autologous bone marrow that has been removed and frozen prior to their chemotherapy; matched allogeneic bone marrow from sibling donors which is phenotypically HLA-identical to the patient; and mismatched allogeneic bone marrow from siblings or other donors which differ at one or more major HLA loci. Even recipients of autologous bone marrow are slow to recover after transplants and frequently platelets and red blood cells are not significantly replenished even in these patients. They are given steroids to reduce inflammation. Patients receiving allogenic bone marrow, either matched or mismatched are subjected to a standard treatment for immunosuppression using cyclosporin and prednisone. For matched allogeneic bone marrow recipients, even when treated with these immunosuppressants show an incidence of GVHD of about 50%. For recipients of mismatched allogeneic bone marrow, immunosuppression is generally effected with cyclosporin in methotrexate with or without prednisone in the standard protocol. In this group of patients, GVHD approaches 90%.

The results below were obtained with each of these three transplantation groups.

A preliminary study was conducted on patients undergoing allogeneic bone marrow transplant for multiple myeloma, for lymphoid malignancies, or for advanced stage CML or AML. Prednisone is often administered as an immunosuppressant in all experimental groups. In the study, these patients received the drugs for a minimum of 3 days to a maximum of 7 days prior to starting their preparative regimen while in the outpatient department according to the following regimen:

PTX: 600 mg p.o. qid at 9 am, 1 pm, 5 pm and 9 pm;

CIPRO: 500 mg p.o.b.i.d.; and

PD: 0.5 mg/kg b.i.d. (total 1 mg/kg/day changed to methylprednisolone at an equivalent dose starting on day−1).

For the duration of therapy, the patients are continued on the study drugs as follows:

PTX: until day +20 post-transplant then tapered 600 mg/day until off;

CIPRO: until day 30 post-transplant or day of discharge if sooner than day 30; and PD: tapered starting on day 0 over 14 days until off.

The following data show the results of this study.

Figure 18:
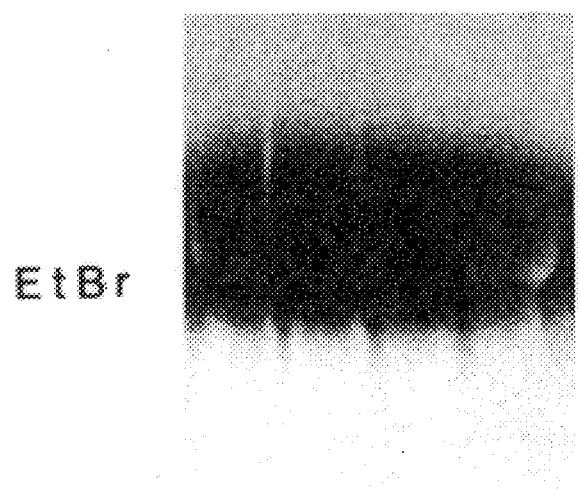
FIG. 18 shows that patients who receive PTX/CIPRO therapy delayed the onset of neutropenia and accelerated engraftment in comparison to patients receiving GM-CSF or PTX alone.

All patients in these studies received PD and cyclosporin as GVHD prophylaxis. Granulocyte recovery was measured post-bone marrow transplant in patients receiving therapy with PTX, CIPRO in addition to standard PD administration (N=10), or GM-CSF (N=10), or PTX (N=4). Therapy with PTX/CIPRO delayed the onset of neutropenia and accelerated engraftment in comparison to that observed in patients receiving GM-CSF or PTX alone. These results are shown in FIG. 18.

In addition, the platelet transfusion requirements and red blood cell requirements during the first 30 days post-transplant were compared in patients receiving GM-CSF (N=27) or therapy with PTX/CIPRO (N=10). In the PTX/CIPRO patients, both requirements were reduced dramatically. For platelet transfusion, PTX/CIPRO patients required only 7.2±5.6 units of platelets as compared to 87±69 units required by the GM-CSF group; the PTX/CIPRO patients required only 4.4±3 units of RBCs as compared to 24.7±24 units of RBCs for the GM/CSF recipients. The time to reach platelet and RBC transfusion independence was also shortened in patients receiving the triple therapy.

Compared to a historical control group or patients receiving GM-CSF, administration of PTX/CIPRO significantly reduced the number of febrile days, maximum bilirubin (liver toxicity) maximum creatinine (kidney toxicity) resulting in a marked reduction in the duration of hospitalization.

The following Tables 2–4 show the results of an extended study using transplant recipients receiving standard treatment, which includes the administration of steroids and/or immunosuppressants as described above, and treatment using PTX/CIPRO. In the case of allogeneic transplants, an additional control group receiving GM-CSF in addition to the immunosuppressants was studied. The legends to the tables explain the various parameters measured. In general, the data are grouped in the tables to show measures of engraftment (ANC), transfusion requirements (Platelets), organ toxicity—creatinine for kidney, bilirubin for liver, and survival.

Table 2 represents the results for autologous recipients. The patients receiving combination therapy with PTX/CIPRO showed enhanced engraftment and survival as compared to patients receiving standard protocols.

Table 3 shows the results for recipients of matched allogeneic donor marrow. Again, engraftment was improved, toxicity diminished and survival improved as compared either to standard treatment or to treatment with GM-CSF.

Table 4 shows the results for recipients of marrow from unrelated donors. Again, the general results were improved as compared to either standard therapy or GM-CSF.

The data in these tables, therefore, indicates that coadministration of pentoxifylline and the quinolone ciprofloxacin generally improves the metabolic status of subjects undergoing bone marrow transplantation as remediation for chemotherapy or irradiation therapy.

TABLE 2

Autologous BMT Trial

|  | Standard Rx | PTX/CIPRO |
|---|---|---|
| # patients | 57 | 21 |
| ANC ≧ 100 | 10.0 (11 ± 5) | 9 (10 ± 2) |
| ANC ≧ 500 | 18.5 (19 ± 8) | 11 (12 ± 5) |
| ANC ≧ 1,000 | 24.0 (22 ± 10) | 14 (15 ± 6) |
| Last plt day | 40.0 (28 ± 15) | 14 (16 ± 9) |
| Units platelets | 88 (96 ± 64) | 40 (47 ± 32) |
| Max Creat (mg/dL) | 1.4 (1.8 ± 1.3) | 1.4 (1.4 ± 0.7) |
| Creat ≧ 2.0 mg/dL | 25% | 14% |
| Max Bili (mg/dL) | 2.7 (7 ± 9) | 1.7 (1.7 ± 2) |
| Bili ≧ 10.0 mg/dL | 17.5% | 0% |
| Day initial discharge | 26.5 (30 ± 12) | 22.5 (25 ± 10) |
| Day 100 Survival | 61% | 92% |
| Relapse Rate | 39% | 10% |
| 1 Year Survival | 33% |  |

| Legend for Autologous Transplants | |
|---|---|
| Autologous Marrow Transplants | Use of bone marrow derived from the patient which is often removed, frozen then re-administered to the patient after the patient has completed a course of radiation and or chemotherapy is referred to as autologous marrow transplantation. Much of the morbidity and mortality seen after BMT is due to the toxic effects of the radiation and chemotherapy to the patients normal cells that make up vital organs like the liver, kidney, lungs and gastrointestinal tract. For example, organ damage, that is damage to kidney, liver, gastrointestinal tract and lungs in the first 21 days after the transplant is most frequently the result of the damaging effects from the high doses of radiation and chemotherapy needed to erradicate the underlying malignant disease (ie leukemia). Because the bone marrow is derived from the patient, there are no immunologic (genetic) differences between the two. This deletes the need for immunsuprressive drugs like cyclosporine and prednisone since conditions like graft vs host disease do not occur in autologous BMT recipients. The ability to protect normal cells from the damaging effects of radiation and chemotherapy is termed chemoprotection. The highest and most lethal doses of radiation and chemotherapy are used in the BMT procedure and as such set the toughest standards by which compounds are judged for their ability to protect cells from the damaging side effects of these agents. |
| Values | median (mean ± standard deviation) |
| p values | Wilcoxon analysis (patients censored at the time of death) Controls/GM-CSF vs PTX/CIPRO |
| ANC | absolute neutrophil count (cells/uL) |
| ≦100 | days below 100 cells/uL |
| ≧100 | day on which ANC ≧100 cells/uL on two consecutive days |
| ≧1,000 | day on which ANC ≧1,000 cells/uL on two consecutive days |
| Last Plt day | First day on which platelet count ≧20,000/uL for 7 consecutive days untransfused |
| Units plts | Total number of units of platelets transfused day 0–28 |
| Max creat | Maximum serum creatinine (mg/dL) day 0–28 post BMT Creatinine is a measurement of kidney function. Normal creatinine ranges from 0.8 to 1.2 mg/dL. A doubling of creatinine implies a 50% reduction in kidney function |
| Creat ≧2.0 | Number (%) of patients with serum creatinine ≧2.0 mg/dL (days 0–28) post BMT. Creatinine ≧2.0 implies a reduction in normal kidney function ≧50% |
| Max Bili | Maximum serum bilirubin (mg/dL 0 days 0–28 post BMT Bilirubin is a measurement of liver function with normal maximum values ≦1.0 mg/dL. |
| Bili ≧10.0 | Number (%) of patients with serum bilirubin ≧10.0 mg/dL (days 0–28) post BMT. Bilirubin ≧10.0 mg/dL implies severe liver of ten fatal liver damage |
| Day discharge | Day of initial discharge from the hospital |
| Day 100 survival | Number (%) of patients alive 100 days post transplant |
| Relapse Rate | Number (%) of patients who survived the procedure but had recurrence (relapse) of their disease. Patients who die from causes other than relapse are censored from this percentage. |
| 1 Year Survival | Number (%) of patients alive 1 year after transplant. |

TABLE 3

MATCHED ALLOGENEIC DONOR TRIAL

| | Standard Rx | GM-CSF | PTX/CIPRO | $p \leq$ |
|---|---|---|---|---|
| # patients | 50 | 27 | 23 | |
| ANC $\leq$100 | 7.0 (6 ± 6) | 5.0 (6 ± 4) | 7 (5 ± 3) | NS |
| ANC $\geq$100 | 8.0 (8 ± 5) | 9.0 (8 ± 6) | 10 (9 ± 4) | NS |
| ANC $\geq$1,000 | 19.0 (21 ± 9) | 14.0 (16 ± 9) | 15 (16 ± 6) | 0.008 |
| Last plt day | 21.0 (38 ± 31) | 23.0 (17 ± 11) | 12 (15 ± 10) | 0.005 |
| Last RBC day | 66.0 (68 ± 51) | 59.0 (63 ± 39) | 15 (15 ± 9) | 0.007 |
| Units platelets | 96.0 (122 ± 63) | 74.0 (87 ± 74) | 21 (31 ± 25) | 0.004 |
| Max Creat (mg/dL) | 1.6 (2.2 ± 1.9) | 1.5 (1.8 ± 1.4) | 1.3 (1.3 ± 0.5) | 0.05 |
| Creat $\geq$2.0 mg/dL | 32% | 22% | 9% | |
| Max Bili (mg/dL) | 3.1 (8 ± 12) | 5.0 (8 ± 10) | 2.1 (2.3 ± 1) | 0.007 |
| Bili $\geq$5.0 mg/dL | 38% | 44% | 0% | |
| Infection 0–28 | 27% | 14% | 13% | |
| Day discharge | 31.0 (36 ± 19) | 24.0 (26 ± 13) | 19 (20 ± 5) | 0.001 |
| Day 100 Survival | 63% | 69% | 87% | 0.01 |

Legend for Matched Allogeneic Transplants

| | |
|---|---|
| Matched Allogeneic BMT | Use of bone marrow derived from sibling donors which are HLA compatible for major histocompatibility antigens A, B, and DR. Unlike autologous BMT, complications that occur after allo-BMT have several contributing factors. For example, organ damage, that is damage to kidney, liver, gastrointestinal tract and lungs in the first 21 days after the transplant is most frequently the result of the damaging effects from the high doses of radiation and chemotherapy needed to erradicate the underlying malignant disease (ie leukemia). However, because the patient and the donor are not genetically identical, a severe immunologic condition called graft vs host disease (GVHD) is frequently seen and contributes to the damage that essential organs like the liver, skin and GI tract often suffer. These damaging effects generally occur after the first 28 days posttransplant and as such can be distinguished from the damage due to direct effects of the chemotherapy |
| Values | median (mean ± standard deviation) |
| p values | Wilcoxon analysis (patients censored at the time of death) Controls/GM-CSF vs PTX/CIPRO |
| ANC | absolute neutrophil count (cells/uL) |
| $\leq$100 | days below 100 cells/uL |
| $\geq$100 | day on which ANC $\geq$100 cells/uL on two consecutive days |
| $\geq$1,000 | day on which ANC $\geq$1,000 cells/uL on two consecutive days |
| Last Plt day | First day on which platelet count $\geq$20,000/uL for 7 consecutive days untransfused |
| Last RBC day | First day on which RBC count $\geq$30% for 7 consecutive days untransfused |
| Units plts | Total number of units of platelets transfused day 0–28 |
| Max creat | Maximum serum creatinine (mg/dL) day 0–28 post BMT Creatinine is a measurement of kidney function. Normal creatinine ranges from 0.8 to 1.2 mg/dL. A doubling of creatinine implies a 50% reduction in kidney function |
| Creat $\geq$2.0 | Number (%) of patients with serum creatinine $\geq$2.0 mg/dL (days 0–28) post BMT. Creatinine $\geq$2.0 implies a reduction in normal kidney function $\geq$50% |
| Max Bili | Maximum serum bilirubin (mg/dL 0 days 0–28 post BMT Bilirubin is a measurement of liver function with normal maximum values $\leq$1.0 mg/dL. |
| Bili $\geq$5.0 | Number (%) of patients with serum bilirubin $\geq$5.0 mg/dL (days 0–28) post BMT. Bilirubin $\geq$5.0 mg/dL implies severe liver damage |
| Infection 0–28 | Percentage of patients with positive bacterial blood cultures days 0–28 post BMT |
| Day discharge | Day of initial discharge from the hospital |
| Day 100 survival | Number (%) of patients alive 100 days post transplant |

TABLE 4

UNRELATED DONOR TRIAL

| | Standard Rx | GM-CSF | PTX/CIPRO |
|---|---|---|---|
| # patients | 78 | 30 | 17 |
| ANC $\leq$100 | 10.5 (10 ± 6) | 12 (12 ± 7) | 11 (10 ± 3) |
| ANC $\geq$100 | 16.0 (17 ± 13) | 18.5 (18 ± 6) | 15 (13 ± 4) |

TABLE 4-continued

| | | | |
|---|---|---|---|
| ANC ≧500 | 21.0 (21 ± 5) | 22.5 (23 ± 4) | 18 (18 ± 4) |
| ANC ≧1,000 | 24.0 (24 ± 7) | 26.0 (26 ± 5) | 21 (20 ± 4) |
| Last plt day | 33.0 (30 ± 17) | 24.5 (26 ± 6) | 20 (23 ± 10) |
| Units platelets | 118 (122 ± 63) | 92.0 (90 ± 42) | 62 (58 ± 23) |
| Max Creat (mg/dL) | 1.4 (1.9 ± 1.5) | 1.1 (1.4 ± 1.2) | 1.6 (1.5 ± 0.3) |
| Creat ≧2.0 mg/dL | 25% | 17% | 17% |
| Max Bili (mg/dL) | 5.8 (12 ± 14) | 5.5 (7 ± 7) | 2.8 (4 ± 3) |
| Bili ≧5.0 mg/dL | 56% | 46% | 23% |
| Infection 0–28 | 27% | 7% | 23% |
| GVHD | | | |
| Grade 0 | 0% | 15% | 35% |
| Grade I | 8% | 8% | 29% |
| Grade II | 40% | 46% | 24% |
| Grade III | 39% | 27% | 12% |
| Grade IV | 13% | 4% | 0% |
| Day initial discharge | 43.0 (40 ± 15) | 37.0 (37 ± 14) | 28 (28 ± 8) |
| Day 100 Survival | 63% | 86% | 84% |

Legend for Unrelated/Mismatched Allogeneic Transplants

| | |
|---|---|
| Unrelated/Mismatched Allogeneic BMT | Use of bone marrow derived from donors other than relatives is referred to as unrelated donor transplants. If the donor bone marrow differs from the patient for major or minor histocompatibility antigens (ie A, B, and DR) it is referred to as mismatched transplants. They can include marrow from related or unrelated donors. Unlike autologous BMT, complications that occur after allo-BMT have several contributing factors. For example, organ damage, that is damage to kidney, liver, gastrointestinal tract and lungs in the first 21 days after the transplant is most frequently the result of the damaging effects from the high doses of radiation and chemotherapy needed to erradicate the underlying malignant disease (ie leukemia). However, because the patient and the donor are not genetically identical, a severe immunologic condition called graft vs host disease (GVHD) is frequently seen and contributes to the damage that essential organs like the liver, skin and GI tract often suffer. Immune suppressing drugs like cyclosposrine, methotrexate and prednisone are often ineffective in preventing GVHD among recipients of mismatched related or unrelated grafts. The incidence of severe GVHD is in excess of 50% despite the use of these agents. These damaging effects generally occur after the first 28 days posttransplant and as such can be distinguished from the damage due to direct effects of the chemotherapy |
| Values | median (mean ± standard deviation) |
| ANC | absolute neutrophil count (cells/uL) |
| ≦100 | days below 100 cells/uL |
| ≧100 | day on which ANC ≧100 cells/uL on two consecutive days |
| ≧1,000 | day on which ANC ≧1,000 cells/uL on two consecutive days |
| Last Plt day | First day on which platelet count ≧20,000/uL for 7 consecutive days untransfused |
| Last RBC day | First day on which RBC count ≧30% for 7 consecutive days untransfused |
| Units plts | Total number of units of platelets transfused day 0–28 |
| Max creat | Maximum serum creatinine (mg/dL) day 0–28 post BMT Creatinine is a measurement of kidney function. Normal creatinine ranges from 0.8 to 1.2 mg/dL. A doubling of creatinine implies a 50% reduction in kidney function |
| Creat ≧2.0 | Number (%) of patients with serum creatinine ≧2.0 mg/dL (days 0–28) post BMT. Creatinine ≧2.0 implies a reduction in normal kidney function ≧50% |
| Max Bili | Maximum serum bilirubin (mg/dL 0 days 0–28 post BMT Bilirubin is a measurement of liver function with normal maximum values ≦1.0 mg/dL. |
| Bili ≧5.0 | Number (%) of patients with serum bilirubin ≧5.0 mg/dL (days 0–28) post BMT. Bilirubin ≧5.0 mg/dL implies severe liver damage |
| Infection 0–28 | Percentage of patients with positive bacterial blood cultures days 0–28 post BMT |
| Day discharge | Day of initial discharge from the hospital |
| Day 100 survival | Number (%) of patients alive 100 days post transplant |

We are claiming that renal side effects (hyperkalemia, localized renal hypertension) and diffuse systemic effects possibly growing out of this renal effect (e.g., hypertension) are derived from stimulation of our pathway in renal mesangial cells and diffusely in endothelial cells; that is to say, a side effect of cyclosporine, due to its membrane active/lipid soluble attributes, is stimulation of lyso-PA acyl transferase and phosphatidate phosphohydrolase (there is direct data available on this from human mesangial cells, endothelial cells, and 3T3 fibroblasts).

Since CT1501 R blocks lyso-PAAT and Ptd Phydr, we are claiming that we can therefore block the acyl transferase/PtdPhydr-induced side effects of Cyclosporine A, including hypertension and renal dysfunction.

We claim:

1. An assay for selecting a therapeutic agent which lowers cellular levels of unsaturated, non-arachidonate phosphatidic acid (PA) and diacylglycerol (DAG) in target cells, comprising:

contacting a first sample of target cells containing PA and DAG with a stimulus which induces increased levels of PA and DAG in the target cell, wherein the target cell is mammalian and derived from mesenchymal, neutrophil or ectodermal embryonic origins or is a transformed cell containing an activated oncogene, a marrow stromal cell or a synaptosome derived from brain cells, or is a subcellular fraction thereof;

determining levels of PA and DAG in said target cells at various time intervals after contacting with the stimulus;

contacting a second sample of said target cells with said stimulus in the presence of a candidate therapeutic agent;

determining levels of said PA and DAG in said second sample of target cells at various time intervals after said contacting; and correlating the levels of said PA and DAG determined in the presence and absence of said candidate therapeutic agent to select the therapeutic agent which lowers cellular levels of said PA or DAG.

2. The method of claim 1 wherein the lower levels of said PA and DAG are a result of inhibition of lysophosphatidic acid acyltransferase or phosphatidic acid phosphohydrolase.

3. The method of claim 1 wherein the stimulus is selected from the group consisting of cytokines, activated oncogenes, antigens, endotoxins, granulocyte macrophage colony stimulating factor (GM-CSF), tumor necrosis factor (TNF), interleukin-1 (IL-1), human immunodeficiency virus (HIV), cytoreductive agents, irradiation, and combinations thereof.

4. The method of claim 3 wherein the stimulus is an agent which inhibits hematopoiesis.

\* \* \* \* \*